United States Patent
Aquila et al.

(10) Patent No.: US 7,049,329 B2
(45) Date of Patent: May 23, 2006

(54) AMINES THAT INHIBIT A MAMMALIAN ANANDAMIDE TRANSPORTER, AND METHODS OF USE THEREOF

(75) Inventors: Brian M. Aquila, Marlborough, MA (US); Seth C. Hopkins, Clinton, MA (US); Curtis A. Lockshin, Lexington, MA (US); Fengjiang Wang, Northborough, MA (US)

(73) Assignee: Sepracor Inc., Marlborough, MA (US)

( * ) Notice: Subject to any disclaimer, the term of this patent is extended or adjusted under 35 U.S.C. 154(b) by 135 days.

(21) Appl. No.: 10/439,347

(22) Filed: May 15, 2003

(65) Prior Publication Data

US 2004/0048907 A1    Mar. 11, 2004

Related U.S. Application Data

(60) Provisional application No. 60/381,041, filed on May 16, 2002.

(51) Int. Cl.
*A61K 31/135*   (2006.01)
*A61K 31/34*    (2006.01)
*A61K 31/44*    (2006.01)
*C07D 307/04*   (2006.01)

(52) U.S. Cl. .............. 514/352; 546/304; 549/429; 564/305; 514/461; 514/649

(58) Field of Classification Search ............... 564/541, 564/152, 153, 161, 164, 162, 163, 305; 514/63, 514/461, 352, 469; 549/429; 546/304
See application file for complete search history.

(56) References Cited

U.S. PATENT DOCUMENTS

| | | | | |
|---|---|---|---|---|
| 2,778,826 | A * | 1/1957 | Schmidle ............... | 546/192 |
| 5,688,825 | A | 11/1997 | Makriyannis et al. ...... | 514/423 |
| 5,874,459 | A | 2/1999 | Makriyannis et al. ...... | 514/425 |
| 5,977,180 | A | 11/1999 | Pate et al. .............. | 514/627 |
| 6,200,951 | B1 * | 3/2001 | Gray et al. .............. | 514/2 |
| 6,335,023 | B1 * | 1/2002 | Yu et al. ............... | 424/401 |
| 6,399,571 | B1 * | 6/2002 | Gray et al. .............. | 514/12 |
| 6,696,412 | B1 * | 2/2004 | Kelleher et al. .......... | 514/9 |
| 2002/0019444 | A1 | 2/2002 | Hogestatt et al. ......... | 514/627 |

FOREIGN PATENT DOCUMENTS

WO      WO 01/92280 A1     12/2001

OTHER PUBLICATIONS

Pirdzhanov et al.,Arylalkylamine derivatives. IV. Synthesis of some substituted phenylrthylamines,,Armyanskii Khimicheskii Zhurnal (1972), 25(6),505-11.*

Schmidle, CJ (1957): STN International, CAPLUS database, Columbus (Ohio), Accession No.: 1957:47302.*
Database CAPLUS on STN, Acc. No. 1939:29763, Blicke, et al., 'Antispasmodics. IV' Journal of the American Chemical Society, (1939), 61, p. 774-6 (abstract, RN=6298-88-0).
International Search Report completed Aug. 23, 2003 and mailed Sep. 18, 2003.
Beltramo et al.; "Reversal of Dopamine $D_2$ Receptor Responses by Anandamide Transport Inhibitor", The Journal of Neuroscience 20(9): 3401-3407, (May 1, 2000).
Beltramo et al.; "Functional Role of High-Affinity Anadaminde Transport, as Revealed by Selective Inhibition", Science 277:1094-1097, (Aug. 22, 1997).
Giuffrida et al.; "Dopamine Activation of Endogenous Cannabinoid Signaling in Dorsal Striatum", Nature Neuroscience 2(4): 358-363, (Apr. 1999).
Giuffrida et al.; "Mechanisms of Endocannabinoid Inactivation: Biochemistry and Pharmacology", The Journal of Pharmacology and Experimental Therapeutics, 298(1): Jul. 14, 2001.
Maccarrone et al.; "Anandamide Hydrolysis by Human Cells in Culture and Brain", The Journal of Biological Chemistry, 273(48): 32332-32339, (Nov. 27, 1998).
Muthian et al.; "Synthesis and Characterization of a Fluorescent Substrate for the N-Arachidonoylethanolamine (Anandamide) Transmembrane Carrier[1]", The Journal of Pharmacology and Experimental Therapeutics, 293(1):289-295 (2000).

(Continued)

*Primary Examiner*—Golam M. M. Shameem
(74) *Attorney, Agent, or Firm*—Dana M. Gordon; Foley Hoag LLP

(57) ABSTRACT

One aspect of the present invention relates to amines. A second aspect of the present invention relates to the use of the amines as inhibitors of a mammalian anandamide transporter. The compounds of the present invention will also find use in the treatment of numerous ailments, conditions and diseases which afflict mammals, including but not limited to asthma, neuropathic pain, persistent pain, inflammatory pain, hyperactivity, hypertension, brain ischemia, Parkinson's disease, spasticity, Tourette's syndrome, schizophrenia, hemorrhagic shock, septic shock, cardiac shock, migrane, Horton's headache, multiple sclerosis, anorexia, AIDS wasting syndrome, organ rejection, autoimmune diseases, allergy, arthritis, Crohn's disease, malignant gliomas, neurodegenerative diseases, Huntington's chorea, glaucoma, nausea, anxiety, psychosis, attention deficit hyperactivity disorder, premature ejaculation, and stroke. Another aspect of the present invention relates to combinatorial libraries of amines, and methods for preparing the libraries.

16 Claims, 6 Drawing Sheets

OTHER PUBLICATIONS

Piomelli et al.; "Structural Determinants for Recognition and Translocation by the Anandamine Transporter", Proc. Natl.Acad. Sci. USA, 96:5802-5807, (May 1999).

Piomelli et al.; "Endogenous Cannabinoid Signaling", Neurobiology of Disease, 5: 462-473, (1998).

Rakhshan et al.; "Carrier-Mediated Uptake of the Endogenous Cannabinoid Anandamine in RBL-2H3 Cells 1", The Journal of Pharmacology and Experimental Therapeutics, 292(3): 960-967, (2000).

Sheskin et al.; "Structural Requirements for Binding of Anandamide-Type Compounds to the Brain Cannabinoid Receptor", J. Med. Chem. 40: 659-667, (1997).

* cited by examiner

Figure 3

| Compound | Inhibition of Anandamide Transporter (IC$_{50}$, nM) |
|---|---|
| | <500 |
| | <500 |
| | <500 |
| | <500 |
| | <500 |

Figure 4

| Compound | Inhibition of Anandamide Transporter (IC$_{50}$, nM) |
|---|---|
| | <1,000 |
| | <500 |
| | <500 |
| | <500 |

Figure 5

| Compound | Inhibition of Anandamide Transporter (IC$_{50}$, nM) |
|---|---|
| | <1,000 |
| | <1,000 |
| | >1,000 |
| | <1,000 |

US 7,049,329 B2

AMINES THAT INHIBIT A MAMMALIAN ANANDAMIDE TRANSPORTER, AND METHODS OF USE THEREOF

RELATED APPLICATIONS

This application claims the benefit of priority to U.S. Provisional Patent Application Ser. No. 60/381,041, filed May 16, 2002.

BACKGROUND OF THE INVENTION

Mammalian Endogenous Cannabinoid System

The various elements of the mammalian endogenous cannabinoid system (ECS) constitute a variety of pharmacological targets for the broad group of compounds generally termed as cannabinoids. Included among these elements are two types of G-protein-coupled membrane receptors: the central $CB_1$ receptors (Matsuda, L. A.; Lolait, S. J.; Brownstein, M. J.; Young, A. C.; Bonner, T. I. Structure of a Cannabinoid Receptor and Functional Expression of the Cloned cDNA. Nature 1990, 346, 561–564); and the peripheral $CB_2$ receptors (Munro, S.; Thomas, K. L.; Abu-Shaar, M. Molecular Characterization of a Peripheral Receptor for Cannabinoids. Nature 1993, 365, 61–65).

Also included among the elements of the ECS are the endogenous ligands anandamide (Devane, W. A.; Hanuš, L.; Breuer, A.; Pertwee, R. G.; Stevenson, L. A.; Griffin, G.; Gibson, D.; Mandelbaum, A.; Etinger, A.; Mechoulam, R. Isolation and Structure of a Brain Constituent That Binds to the Cannabinoid Receptor. Science 1992, 258, 1946–1949), 2-arachidonoylglycerol (Sugiura, T.; Kondo, S.; Sukagawa, A.; Nakane, S.; Shinoda, A.; Itoh, K; Yamashita, A.; Waku, K. 2-Arachidonoylglycerol: a Possible Endogenous Cannabinoid Receptor Ligand in Brain. Biochem. Biophys. Res. Commun. 1995, 215, 89–97), and the recently reported 2-arachidonyl glyceryl ether (Hanuš, L.; Abu-Lafi, S.; Fride, E.; Breuer, A.; Vogel, Z.; Shalev, D. E.; Kustanovich, I.; Mechoulam, R. 2-Arachidonyl Glyceryl Ether, an Endogenous Agonist of the Cannabinoid CBI Receptor. Proc. Natl. Acad. Sci. U.S.A. 2001, 98, 3662–3665). A mechanism for the termination of the biological activity of the endogenous ligands has been elucidated, composed of a carrier-mediated transport system (anandamide transporter (AT)) and a hydrolyzing enzyme, named fatty acid amide hydrolase (FAAH). Hillard, C. J.; Edgemond, W. S.; Jarrahian, A; Campbell, W. B. Accumulation of N-Arachidonoylehanolamine (Anandamide) into Cerebellar Granule Cells Occurs via Facilitated Diffusion. J. Neurochem. 1997, 69, 631–638; Beltramo, M.; Stella, N.; Calignano, A.; Lin, S. Y.; Makriyannis, A.; Piomelli, D. Functional Role of High-Affinity Anandamide Transport, as Revealed by Selective Inhibition. Science 1997, 277, 1094–1097; Hillard, C. J.; Jarrahian, A. The Movement of N-arachidonoylethanolamine (Anandamide) across Cellular Membranes. Chem. Phys. Lipids 2000, 108, 123–134; and Ueda, N.; Puffenbarger, R. A.; Yamamoto, S.; Deutsch, D. G. The Fatty Acid Amide Hydrolase (FAAH). Chem. Phys. Lipids 2000, 108, 107–121.

Importantly, the ECS seems to be involved in the regulation of a wide variety of central and peripheral processes, such as anti-nociception, brain development, retrograde neuronal communication, memory, appetite, psychomotor control, cardiovascular and immune regulation, and cellular proliferation. See (a) Calignano, A.; La Rana, G.; Giuffrida, A.; Piomelli, D. Control of Paul Initiation by Endogenous Cannabinoids. Nature 1998, 394, 277–281; (b) Walker, J. M.; Hohmann, A. G.; Martin, W. J.; Strangman, N. M.; Huang, S. M.; Tsou, K The Neurobiology of Cannabinoid Analgesia. Life Sci. 1999, 65, 665–673; (c) Fernández-Ruiz, J.; Berrendero, F.; Hernádndez, M. L.; Ramos, J. A. The Endogenous Cannabinoid System and Brain Development. Trends Neurosci. 2000, 23, 14–20; (d) Wilson, R. I.; Nicoll, R. A.; Endogenous Cannabinoids Mediate Retrograde Signaling at Hippocampal Synapses. Nature 2001, 410, 588–592; (e) Hampson, R. E.; Deadwyler, S. A. Cannabinoids, Hippocampal Function and Memory. Life Sci. 1999, 65, 715–723; (f) Di Marzo, V.; Goparaju, S. K; Wang, L.; Liu, J.; Bátkai, S.; Járai, Z.; Fezza, F.; Miura, G. I.; Palmiter, R. D.; Sugiura, T.; Kunos, G. Leptin-Regulated Endocannabinoids Are Involved in Maintaining Food Intake. Nature 2001, 410, 822–825; (g) Giuffrida, A.; Piomelli, D. The Endocannabinoid System: a Physiological Perspective on its Role in Psychomotor Control. Chem. Phys. Lipids 2000, 108, 151–158; and (h) De Petrocellis, L.; Melck, D.; Bisogno, T.; Di Marzo, V. Endocannabinoids and Fatty Acid Amides in Cancer, Inflammation and Related Disorders. Chem. Phys. Lipids 2000, 108, 191–209. This broad spectrum of action makes the ECS an important therapeutic target for the treatment of diverse pathologies, including asthma, pain, multiple sclerosis, malignant gliomas, and neurodegenerative diseases. See (a) Calignano, A.; Kátona, I.; Desamaud, F.; Giuffrida, A.; La Rana, G.; Mackie, K; Freund, T. F.; Piomelli, D. Bidirectional Control of Airway Responsiveness by Endogenous Cannabinoids. Nature 2000, 408, 96–101; (b) Baker, D.; Pryce, G.; Croxford, J. L.; Brown, P.; Pertwee, R. G.; Huffman, J. W.; Layward, L. Cannabinoids Control Spasticity and Tremor in a Multiple Sclerosis Model. Nature 2000, 404, 84–87; (c) Galve-Roperh, I.; Sanchez, C.; Cortés, M. L.; Gomez del Pulgar, T.; Izquierdo, M.; Guzman, M. Antitumoral Action of Cannabinoids: Involvement of Sustained Ceramide Accumulation and Extracellular Signal-Regulated Kinase Activation. Nat. Med. 2000, 6, 313–319; and (d) Pertwee, R. G. Pharmacology of Cannabinoid Receptor Ligands. Curr. Med. Chem. 1999, 6, 635–664.

Moreover, an increased level of endocannabinoids in mammalian cells can be obtained by inhibiting their uptake and/or degradation, raising the possibility of producing local cannabimimetic effects without directly activating cannabinoid receptors with classic agonists, thereby avoiding their associated undesirable side effects. Therefore, synthetic inhibitors may be of potential therapeutic value for the treatment of disorders characterized by a low endocannabinoid activity and where direct agonists have proven to be effective, yet produce undesirable effects. Piomelli, D.; Giuffrida, A.; Calignano, A; Rodriguez de Fonseca, F. The Endocannabinoid System as a Target for Therapeutic Drugs. Trends Pharmacol. Sci. 2000, 21, 218–224. In particular, the therapeutic utility of such uptake inhibitors has been considered for the treatment of diverse pathologies as Huntington's chorea or multiple sclerosis . Baker, D.; Pryce, G.; Croxford, J. L.; Brown, P.; Pertwee, R. G.; Makriyannis, A.; Khanolkar, A.; Layward, L.; Fezza, F.; Bisogno, T; Di Marzo, V. Endocannabinoids Control Spasticity in a Multiple Sclerosis Model. FASEB J. 2001, 15, 300–302.

Anandamide

Generally, cannabinoid agonists include both exogenous active molecules as well as endocannabinoids. Exogenous agonists are usually classified as classical cannabinoids (Cannabis sativa derived compounds as, for example, $\Delta^9$-THC and their analogues), nonclassical cannabinoids (which lack the characteristic tricyclic structure of classical ones, as, for instance, CP55940), and aminoalkylindoles (e.g., WIN552122), whereas endogenous cannabinoids belong to the eicosanoid class. Among the antagonists, diarylpyrazoles merit special mention as being the most widely used compounds. Pertwee, R. G. Cannabinoid Receptor Ligands: Clinical and Neuropharmacological Considerations, Relevant to Future Drug Discovery and Development. *Expert Opin. Invest. Drugs* 2000, 9, 1–19.

Anandamide (arachidonylethanolamide) is an endogenous lipid that activates brain cannabinoid receptors and mimics the pharmacological effects of $\Delta^9$-tetrahydrocannabinol, the active principle of hashish and marijuana. W. A. Devane et at., *Science* 258, 1946 (1992); and R. Mechoulam, L. Hanus, B. R. Martin, *Biochem. Pharmacol.* 48, 1537 (1994). In humans, such effects include euphoria, calmness, dream states, and drowsiness. W. L. Dewey, *Pharmacol. Rev.* 38, 151 (1986). Depolarized neurons release anandamide through a mechanism that may require the calcium-dependent cleavage of a phospholipid precursor in neuronal membranes. V. Di Marzo et al., *Nature* 372, 686 (1994); and H. Cadas, S. GaiUet, M. Bettramo, L. Venance, D. Piomelli, *J. Neurosci.* 16, 3934 (1996); T. Sugiura et al., *Eur. J Biochem.* 240, 53 (1996); and H. Cadas, E. di Tomaso, D. Piomelli, *J. Neurosci.*, 17, 1226 (1997). Moreover, anandamide may act as the chief component of a novel system involved in the control of cognition and emotion. In fact, physiological experiments have shown that anandamide may be as important in regulating our brain functions in health and disease as other better-understood neurotransmitters, such as dopamine and serotonin.

Anandamide is released from membrane compartments in neurons in response to receptor stimulation. Notably, D2 agonism stimulates anandamide release. In studies of rat brain neurons, anandamide was determined to be released by a unique mechanism: it is stored in the cell membrane in the form of a phospholipid precursor, which is cleaved by a calcium—and activity-dependent enzymatic reaction. N-arachidonoyl phosphatidylethanolamine (NAPE) has been identified as a precursor for anandamide, which is formed by a phosphodiesterase-mediated cleavage of NAPE. The biosynthesis of NAPE is catalyzed by an N-acyltransferase enzyme, which has been characterized and partially purified from rat brain extracts. The formation of NAPE and its cleavage to yield anandamide are highly regulated processes, which take place in select regions of the brain.

Like other modulatory substances, extracellular anandamide is thought to be rapidly inactivated. As outlined in the preceding section, the pathway involves hydrolysis to arachidonic acid and ethanolamine, catalyzed by a membrane-bound fatty acid amide hydrolase (FAAH) highly expressed in rat brain and liver. D. G. Deutsch and S. Chin, *Biochem. Pharmacol.* 46, 791 (1993); F. Desamaud, H. Cadas, O. Piomelli, *J. Biol. Chem.* 270, 6030 (1995). Nevertheless, the low FAAH activity found in brain plasma membranes indicates that this enzyme may be intracellular, a possibility that is further supported by sequence analysis of rat FAAH. B. Cravatt et al., *Nature* 384, 83 (1996). Although anandamide could gain access to FAAH by passive diffusion, the transfer rate by this mechanism is expected to be low due to the molecular size of this lipid mediator. W. D. Stein, *Channels and Pumps. An Introduction to Membrane Transport*, (Academic Press, San Diego, 1990), pp. 53–57. Other lipids, including polyunsaturated fatty acids and prostaglandin $E_2$ ($PGE_2$), enter cells by carrier-mediated transport (L. Z. Bito, *Nature* 256, 1234 (1975); J. E. Schaffer and H. F. Lodish, *Cell* 79, 427 (1994); I. N. Bojesen and E. Bojesen, *Acta PhysioL Scand.* 156, 501 (1996); N. Kanai et al., *Science* 268, 866 (1995)). As mentioned above, a rapid, saturable process of anandamide accumulation, via the anandamide transporter, into neural cells has been reported. V. Di Marzo et al., *Nature* 372, 686 (1994).

The inactivation of anandamide, necessary to terminate its biological effects, occurs in two steps. It is first removed from the extracellular space by a selective carrier protein that transports it into cells, where it is then broken down by hydrolysis, catalyzed by the enzyme anandamide amidohydrolase, into biologically inactive compounds. A potent inhibitor of this enzyme has been identified (a bromoenol lactone, BTNP), and its availability will facilitate pharmacological analysis of anandamide action. A high-affinity anandamide transporter has been characterized in rat cortical neurons and in astrocytes. A compound (N-(4-hydroxyphenyl)arachidonylamide) has been found that selectively and potently inhibits such transport, without binding to cannabinoid receptors or affecting anandamide hydrolysis. This transport system appears to constitute a novel lipid uptake system analogous to, but distinct from, the prostaglandin uptake system. Also, the use of these inhibitors allowed the demonstration that anandamide transport constitutes the rate-limiting step in the biological inactivation of anandamide, both in vitro and in vivo. It is important to understand how anandamide levels are regulated, because a deregulation may lead to brain dysfunction.

Anandamide and dopamine appear to act in opposite ways to control movements in an area of the brain called the dorsal striatum; dopamine stimulates movements by acting in this area, and anandamide apparently inhibits this action of dopamine. The determination that anandamide can counteract dopamine will prove useful in the development of medications for treating diseases that seem to involve dopamine inbalances in the brain. Certain diseases appear to be caused by too much dopamine in certain brain regions, or perhaps hypersensitivity of brain sites targeted by dopamine. These diseases include schizophrenia and Gilles de la Tourette syndrome, which is characterized by facial tics, repeating of words and phrases, and uncontrollable shouting of obscenities. Medications that mimic anandamide might reduce the symptoms of these and other diseases by dampening dopamine overactivity. Additionally, medications that block anandamide action in the brain should also prove useful in treating diseases that appear to be associated with too little dopamine in certain brain regions, or hyposensitivity of dopamine targets. These diseases include drug addiction and Parkinson's disease.

In rats, AM404, an AT inhibitor, prolongs the lifetime of released anandamide in the brain and reduces the psychomotor effects of dopamine D2 agonism. Painful stimuli in rats causes anandamide release that mediates a natural analgesic response in the dorsal lateral periaqueductal gray region of the brain via agonism of CB1 receptors. In various in vivo models, AM404 produced mild, slowly developing hypokinesia that was reversible by the cannabinoid CB1 receptor antagonist SR-141716A. AM404 also prevented apomorphine-induced yawning in a dose dependent manner; this effect was likewise reversed by SR-141716A. Moreover, AM404 decreased the motor behavior stimulation induced by quinpirole, a selective dopamine D2 agonist, and reduced hyperactivity in a rat model of ADHD. AM404 inhibits AT ($IC_{50}$~2 μM), but is not suitable for drug candidacy due to its low potency and specificity. The latter characteristic is likely due to its arachinonyl moeity. Additionally, using in vitro assays, researchers have shown that phenylmethylsulfonyl fluoride (PMSF) can inhibit the degradation of anandamide. Further, a series of fatty acid sulfonyl fluorides have been identified that inhibit amidase and are more potent and selective than PMSF. Deutsch, D.G. et al. "Fatty acid sulfonyl fluorides inhibit anandamide metabolism and bind to the cannabinoid receptor" *Biochemical and Biophysical Research Communications* 1997, 231, 217–221.

Interestingly, anandamide and structurally related lipids have recently been reported to modulate the activity of vanilloid receptors on primary sensory nerves. U.S. Patent Application Publication No. US 2002/0019444 A1. This discovery has numerous implications in the medical, pharmaceutical, and scientific fields, and provides a molecular mechanism for the non-CB1 receptor-mediated vasodilator action of anandamide. The vanilloid receptor (VR1), which was recently cloned by Caterina et al. (Caterina, M. J. et al., The capsaicin receptor: a heat-activated ion channel in the pain pathway., *Nature* 389, 816–824 (1997)), is a capsaicin-sensitive, heat-gated, non-selective cation channel. The work by Caterina et al. and subsequent studies have confirmed that VR1 is uniquely expressed in a subset of primary sensory neurons (Tominaga K, Caterina M J, Mahnberg A B, Rosen T A, Gilbert H, Skinner K, Raumann B E, Basbaum A I, Julius D., The cloned capsaicin receptor integrates multiple pain-producing stimuli., *Neuron* 21, 531–543 (1998)), which are widely distributed in the humans and animals (Holzer P., Capsaicin: cellular targets, mechanisms of action, and selectivity for thin sensory neurons, *Pharmacol Rev* 43, 143–201 (1991)).

SUMMARY OF THE INVENTION

One aspect of the present invention relates to amines. A second aspect of the present invention relates to the use of the amines as inhibitors of a mammalian anandamide transporter. The compounds of the present invention will also find use in the treatment of numerous ailments, conditions and diseases which afflict mammals, including but not limited to asthma, neuropathic pain, persistent pain, inflammatory pain, hyperactivity, hypertension, brain ischemia, Parkinson's disease, spasticity, Tourette's syndrome, schizophrenia, hemorrhagic shock, septic shock, cardiac shock, migrane, Horton's headache, multiple sclerosis, anorexia, AIDS wasting syndrome, organ rejection, autoimmune diseases, allergy, arthritis, Crohn's disease, malignant gliomas, neurodegenerative diseases, Huntington's chorea, glaucoma, nausea, anxiety, psychosis, attention deficit hyperactivity disorder, premature ejaculation, and stroke. Another aspect of the present invention relates to combinatorial libraries of amines, and methods for preparing the libraries.

BRIEF DESCRIPTION OF THE FIGURES

FIG. 3 depicts certain compounds of the present invention and their $IC_{50}$ values against a mammalian anandamide transporter, determined using the assay described in Example 5.

FIG. 4 depicts certain compounds of the present invention and their $IC_{50}$ values against a mammalian anandamide transporter, determined using the assay described in Example 5.

FIG. 5 depicts certain compounds of the present invention and their $IC_{50}$ values against a mammalian anandamide transporter, determined using the assay described in Example 5.

DETAILED DESCRIPTION OF THE INVENTION

Figure 1:
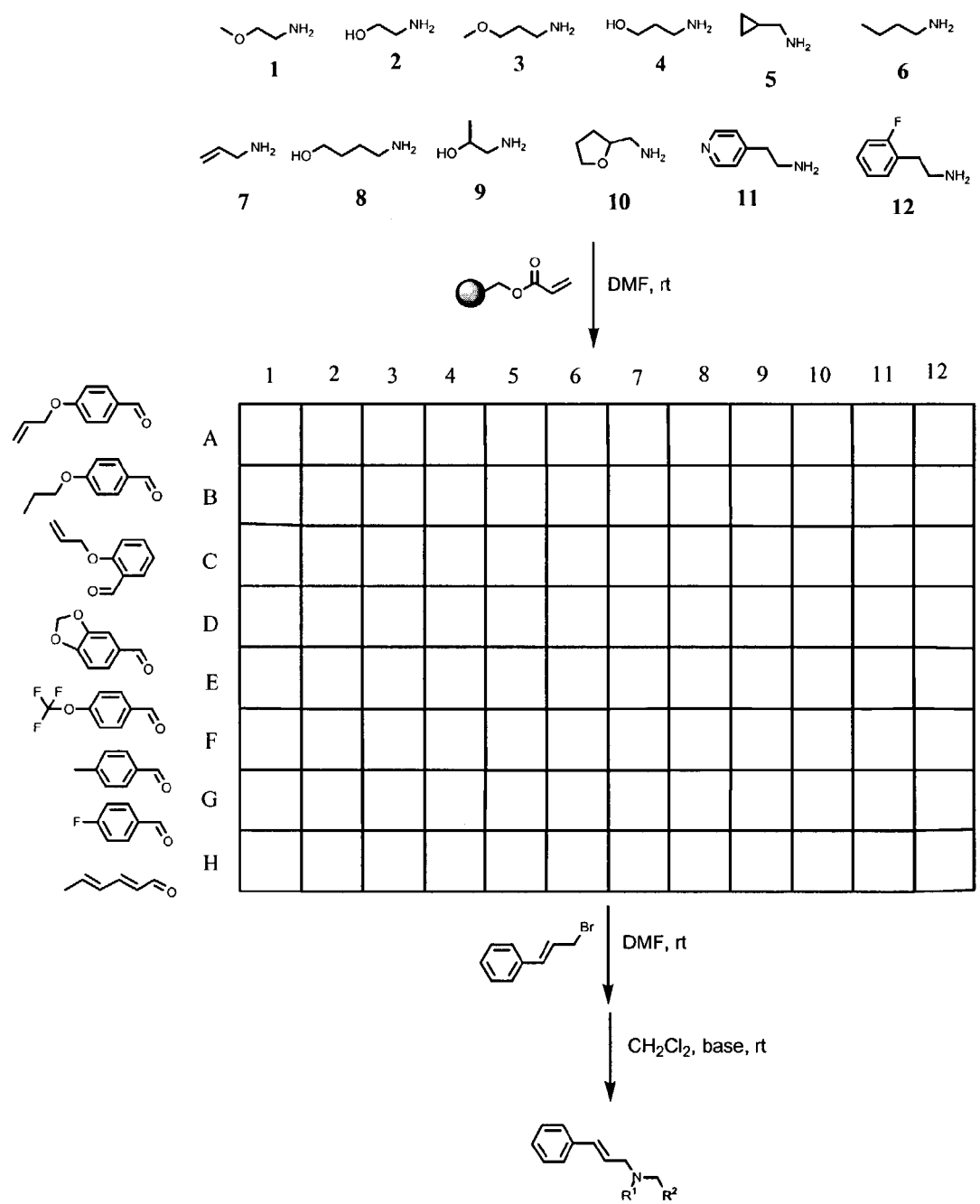
FIG. 1 depicts schematically the synthesis and ninety-six members of a combinatorial library of anandamide transporter inhibitors comprising a cinnamyl moiety.

We have discovered that the therapeutic benefits of cannabinoid agonism can be prolonged by extending the extraneuronal lifetime of released anandamide. Psychosis that is characterized by hyperfunctioning of D2 receptors is attenuated by negative feedback via anandamide release, and can be prevented by prolonging the extraneuronal lifetime of anandamide.

One aspect of the present invention relates to novel amines. A second aspect of the present invention relates to the use of the novel amines as inhibitors of a mammalian anandamide transporter. The compounds of the present invention will also find use in the treatment of numerous ailments, conditions and diseases which afflict mammals, including but not limited to asthma, neuropathic pain, persistent pain, inflammatory pain, hyperactivity, hypertension, brain ischemia, Parkinson's disease, spasticity, Tourette's syndrome, schizophrenia, hemorrhagic shock, septic shock, cardiac shock, migrane, Horton's headache, multiple sclerosis, anorexia, AIDS wasting syndrome, organ rejection, autoimmune diseases, allergy, arthritis, Crohn's disease, malignant gliomas, neurodegenerative diseases, Huntington's chorea, glaucoma, nausea, anxiety, psychosis, attention deficit hyperactivity disorder, premature ejaculation, and stroke. Another aspect of the present invention relates to combinatorial libraries of the novel amines, and methods for preparing the libraries.

DEFINITIONS

For convenience, certain terms employed in the specification, examples, and appended claims are collected here.

The term "anandamide" refers to N-(2-hydroxyethyl)arachidonamide, which has the following structure:

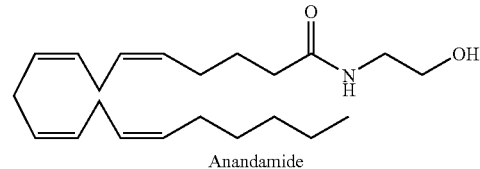

Anandamide

The terms "AM404" and "AM-404" refer to N-(4-hydroxyphenyl)arachidonamide, which has the following structure:

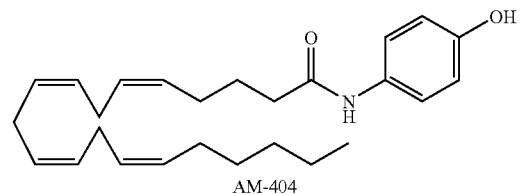

AM-404

The term "cell surface proteins" includes molecules that occur on the surface of cells, interact with the extracellular environment, and transmit or transduce information regarding the environment intracellularly.

The term "extracellular signals" includes a molecule or a change in the environment that is transduced intracellularly via cell surface proteins that interact, directly or indirectly, with the signal. An extracellular signal is any compound or substance that in some manner specifically alters the activity of a cell surface protein. Examples of such signals include, but are not limited to, molecules such as acetylcholine, growth factors, hormones and other mitogenic substances, such as phorbol mistric acetate (PMA), that bind to cell surface receptors and ion channels and modulate the activity of such receptors and channels. Extracellular signals also includes as yet unidentified substances that modulate the activity of a cell surface protein and thereby affect intracellular functions and that are potential pharmacological agents that may be used to treat specific diseases by modulating the activity of specific cell surface receptors.

The term "$ED_{50}$" means the dose of a drug which produces 50% of its maximum response or effect. Alternatively, the dose which produces a pre-determined response in 50% of test subjects or preparations.

The term "$LD_{50}$" means the dose of a drug which is lethal in 50% of test subjects.

The term "therapeutic index" refers to the therapeutic index of a drug defined as $LD_{50}/ED_{50}$.

The term "structure-activity relationship (SAR)" refers to the way in which altering the molecular structure of drugs alters their interaction with a receptor, enzyme, etc.

The term "agonist" refers to a compound that mimics the action of natural transmitter or, when the natural transmitter is not known, causes changes at the receptor complex in the absence of other receptor ligands.

The term "antagonist" refers to a compound that binds to a receptor site, but does not cause any physiological changes unless another receptor ligand is present.

The term "competitive antagonist" refers to a compound that binds to a receptor site; its effects can be overcome by increased concentration of the agonist.

The term "partial agonist" refers to a compound that binds to a receptor site but does not produce the maximal effect regardless of its concentration.

The term "inverse agonist" refers to a compound that binds to a constitutively active receptor site and reduces its physiological function.

The term "ligand" refers to a compound that binds at the receptor site.

The term "heteroatom" as used herein means an atom of any element other than carbon or hydrogen. Preferred heteroatoms are boron, nitrogen, oxygen, phosphorus, sulfur and selenium.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma (σ) constant. This well known constant is described in many references, for instance, J. March, *Advanced Organic Chemistry*, McGraw Hill Book Company, New York, (1977 edition) pp. 251–259. The Hammett constant values are generally negative for electron donating groups (σ[P]=−0.66 for $NH_2$) and positive for electron withdrawing groups (σ[P]=0.78 for a nitro group), σ[P] indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics" The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, azetidine, azepine, thiophene, thianthrene, furan, pyran, isobenzofuran, chromene, xanthene, phenoxathin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

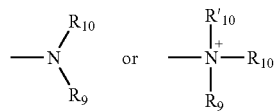

wherein $R_9$, $R_{10}$ and $R'_{10}$ each independently represent a group permitted by the rules of valence.

The term "acylamino" is art-recognized and refers to a moiety that can be represented by the general formula:

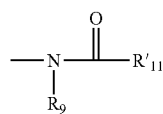

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

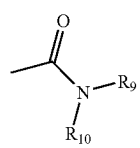

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

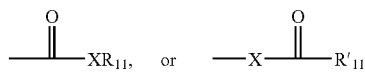

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

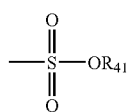

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The term "sulfate" is art recognized and includes a moiety that can be represented by the general formula:

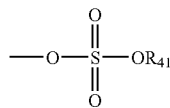

in which $R_{41}$ is as defined above.

The term "sulfonylamino" is art recognized and includes a moiety that can be represented by the general formula:

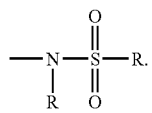

The term "sulfamoyl" is art-recognized and includes a moiety that can be represented by the general formula:

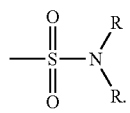

The term "sulfonyl", as used herein, refers to a moiety that can be represented by the general formula:

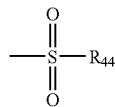

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

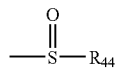

in which $R_{44}$ is selected from the group consisting of hydrogen, alkyl, alkenyl, alkynyl, cycloalkyl, heterocyclyl, aralkyl, or aryl.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W. ; Wuts, P. G. M. *Protective Groups in Organic Synthesis*, 2$^{nd}$ ed.; Wiley: N.Y., 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, it may be isolated using chiral chromatography methods, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as analgesics), wherein one or more simple variations of substituents are made which do not adversely affect the efficacy of the compound in binding to opioid receptors. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986–87, inside cover.

Compounds of the Invention

In certain embodiments, a compound of the present invention is represented by A:

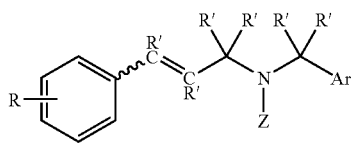

wherein

Z represents alkyl, cycloalkyl, alkenyl, aralkyl, heteroaralkyl, hydroxyalkyl, alkoxyalkyl, heterocyclyl, —$(CH_2)_n$—$R_{80}$, or a covalent tether to a solid support;

Ar represents aryl or heteroaryl;

R is absent or present 1, 2, 3, 4, or 5 times;

R represents independently for each occurrence alkyl, cycloalkyl, alkenyl, alkynyl, aryl, heteroaryl, aralkyl, halogen, heteroaralkyl, hydroxyl, alkoxyl, amino, alkylamino, carboxylate, carboxamide, nitroso, nitro, sulfhydryl, alkylthio, thioalkyl, silyl, alkylsulfonyl, arylsulfonyl, formyl, acyl, acyloxy, acylamino, alkyloxycarbonyl, alkenyloxycarbonyl, aryloxycarbonyl, or —$(CH_2)_n$—$R_{80}$;

R' represents independently for each occurrence H, alkyl, cycloalkyl, aryl, heteroaryl, aralkyl, heteroaralkyl, or —$(CH_2)_n$—$R_{80}$;

$R_{80}$ represents independently for each occurrence cycloalkyl, alkenyl, aryl, heteroaryl, or heterocyclyl;

n is an integer selected independently for each occurrence from the range 0 to 8 inclusive;

the absolute stereochemistry at a stereocenter in a compound represented by A is R, S, or a mixture thereof; and the configuration of an alkenyl moiety in a compound represented by A is E, Z, or a mixture thereof.

In certain embodiments, a compound of the present invention is represented by A and the attendant definitions, wherein Z represents 2-methoxyethyl, 2-hydroxyethyl, 3-methoxypropyl, 3-hydroxypropyl, cyclopropyl, cyclopropylmethyl, 2-methylpropyl, butyl, allyl, 4-hydroxybutyl, 2-hydroxypropyl, (tetrahydrofuran-2-yl)methyl, 2-(pyrid-4-yl)ethyl, or 2-(2-fluorophenyl)ethyl.

In certain embodiments, a compound of the present invention is represented by A and the attendant definitions, wherein Ar represents 4-allyloxyphenyl, 4-propyloxyphenyl, 2-allyloxyphenyl, 3,4-(methylenedioxy)phenyl, 4-(trifluoromethoxy)phenyl, 4-methylphenyl, 4-methoxyphenyl, 4-carboxyphenyl, or 4-fluorophenyl.

In certain embodiments, a compound of the present invention is represented by A and the attendant definitions, wherein R is absent.

In certain embodiments, a compound of the present invention is represented by A and the attendant definitions, wherein R' represents H.

In certain embodiments, a compound of the present invention is represented by A and the attendant definitions, wherein Z represents 2-methoxyethyl, 2-hydroxyethyl, 3-methoxypropyl, 3-hydroxypropyl, cyclopropyl, cyclopropylmethyl, 2-methylpropyl, butyl, allyl, 4-hydroxybutyl, 2-hydroxypropyl, (tetrahydrofuran-2-yl)methyl, 2-(pyrid-4-yl)ethyl, or 2-(2-fluorophenyl)ethyl; and Ar represents 4-allyloxyphenyl, 4-propyloxyphenyl, 2-allyloxyphenyl, 3,4-(methylenedioxy)phenyl, 4-(trifluoromethoxy)phenyl, 4-methylphenyl, 4-methoxyphenyl, 4-carboxyphenyl, or 4-fluorophenyl.

In certain embodiments, a compound of the present invention is represented by A and the attendant definitions, wherein Z represents 2-methoxyethyl, 2-hydroxyethyl, 3-methoxypropyl, 3-hydroxypropyl, cyclopropyl, cyclopropylmethyl, 2-methylpropyl, butyl, allyl, 4-hydroxybutyl, 2-hydroxypropyl, (tetrahydrofuran-2-yl)methyl, 2-(pyrid-4-yl)ethyl, or 2-(2-fluorophenyl)ethyl; Ar represents 4-allyloxyphenyl, 4-propyloxyphenyl, 2-allyloxyphenyl, 3,4-(methylenedioxy)phenyl, 4-(trifluoromethoxy)phenyl, 4-methylphenyl, 4-methoxyphenyl, 4-carboxyphenyl, or 4-fluorophenyl; and R is absent.

In certain embodiments, a compound of the present invention is represented by A and the attendant definitions, wherein Z represents 2-methoxyethyl, 2-hydroxyethyl, 3-methoxypropyl, 3-hydroxypropyl, cyclopropyl, cyclopropylmethyl, 2-methylpropyl, butyl, allyl, 4-hydroxybutyl, 2-hydroxypropyl, (tetrahydrofuran-2-yl)methyl, 2-(pyrid-4-yl)ethyl, or 2-(2-fluorophenyl)ethyl; Ar represents 4-allyloxyphenyl, 4-propyloxyphenyl, 2-allyloxyphenyl, 3,4-(methylenedioxy)phenyl, 4-(trifluoromethoxy)phenyl, 4-methylphenyl, 4-methoxyphenyl, 4-carboxyphenyl, or 4-fluorophenyl; R is absent.

In certain embodiments, a compound of the present invention is represented by A and the attendant definition, wherein Z represents 2-methoxyethyl, 2-hydroxyethyl, 3-methoxypropyl, 3-hydroxypropyl, cyclopropyl, cyclopropylmethyl, 2-methylpropyl, butyl, allyl, 4-hydroxybutyl, 2-hydroxypropyl, (tetrahydrofuran-2-yl)methyl, 2-(pyrid-4-yl)ethyl, or 2-(2-fluorophenyl)ethyl; Ar represents 4-allyloxyphenyl, 4-propyloxyphenyl, 2-allyloxyphenyl, 3,4-(methylenedioxy)phenyl, 4-(trifluoromethoxy)phenyl, 4-methylphenyl, 4-methoxyphenyl, 4-carboxyphenyl, or 4-fluorophenyl; R is absent; and R' represents H.

In assays based on a mammalian anandamide transporter, certain compounds according to structure A have $IC_{50}$ values less than 1 µM, more preferably less than 100 nM, and most preferably less than 10 nM.

In assays based on a mammalian anandamide transporter, certain compounds according to structure A have $EC_{50}$ values less than 1 µM, more preferably less than 100 nM, and most preferably less than 10 nM.

In certain embodiments, a compound of the present invention is represented by B:

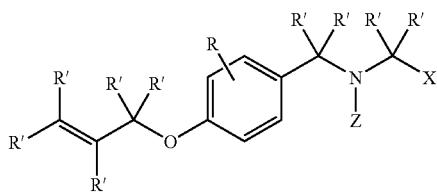

wherein

Z represents alkyl, cycloalkyl, alkenyl, aralkyl, heteroaralkyl, hydroxyalkyl, alkoxyalkyl, heterocyclyl, —$(CH_2)_n$—$R_{80}$, or a covalent tether to a solid support;

X represents aryl, heteroaryl, (aryl)alkenyl, (heteroaryl)alkenyl, or —$(CH_2)_n$—$R_{80}$;

R is absent or present 1, 2, 3, or 4 times;

R represents independently for each occurrence alkyl, cycloalkyl, alkenyl, alkynyl, aryl, heteroaryl, aralkyl, halogen, heteroaralkyl, hydroxyl, alkoxyl, amino, alkylamino, carboxylate, carboxamide, nitroso, nitro, sulfhydryl, alkylthio, thioalkyl, silyl, alkylsulfonyl, arylsulfonyl, formyl, acyl, acyloxy, acylamino, alkyloxycarbonyl, alkenyloxycarbonyl, aryloxycarbonyl, or —$(CH_2)_n$—$R_{80}$;

R' represents independently for each occurrence H, alkyl, cycloalkyl, aryl, heteroaryl, aralkyl, heteroaralkyl, or —$(CH_2)_n$—$R_{80}$;

$R_{80}$ represents independently for each occurrence cycloalkyl, alkenyl, aryl, heteroaryl, or heterocyclyl;

n is an integer selected independently for each occurrence from the range 0 to 8 inclusive;

the absolute stereochemistry at a stereocenter in a compound represented by B is R, S, or a mixture thereof; and the configuration of an alkenyl moiety in a compound represented by B is E, Z, or a mixture thereof.

In certain embodiments, a compound of the present invention is represented by B and the attendant definitions, wherein Z represents 2-methoxyethyl, 2-hydroxyethyl, 3-methoxypropyl, 3-hydroxypropyl, cyclopropyl, cyclopropylmethyl, ethyl, allyl, 4-hydroxybutyl, 2-hydroxypropyl, (tetrahydrofuran-2-yl)methyl, or 2-(2-fluorophenyl)ethyl.

In certain embodiments, a compound of the present invention is represented by B and the attendant definitions, wherein X represents 2-phenylethyl, (E)-(2-methoxyphenyl)CH~CH—, 4-allyloxyphenyl, 3,4-(methylenedioxy)phenyl, (E)-(4-methoxyphenyl)CH~CH—, 4-fluorophenyl, 3,4-difluorophenyl, or 4-(trifluoromethoxy)phenyl.

In certain embodiments, a compound of the present invention is represented by B and the attendant definitions, wherein R is absent.

In certain embodiments, a compound of the present invention is represented by B and the attendant definitions, wherein R' represents H.

In certain embodiments, a compound of the present invention is represented by B and the attendant definitions, wherein Z represents 2-methoxyethyl, 2-hydroxyethyl, 3-methoxypropyl, 3-hydroxypropyl, cyclopropyl, cyclopropylmethyl, ethyl, allyl, 4-hydroxybutyl, 2-hydroxypropyl, (tetrahydrofuran-2-yl)methyl, or 2-(2-fluorophenyl)ethyl; and X represents 2-phenylethyl, (E)-(2-methoxyphenyl)CH~CH—, 4-allyloxyphenyl, 3,4-(methylenedioxy)phenyl, (E)-(4-methoxyphenyl)CH~CH—, 4-fluorophenyl, 3,4-difluorophenyl, or 4-(trifluoromethoxy)phenyl.

In certain embodiments, a compound of the present invention is represented by A and the attendant definitions, wherein Z represents 2-methoxyethyl, 2-hydroxyethyl, 3-methoxypropyl, 3-hydroxypropyl, cyclopropyl, cyclopropylmethyl, ethyl, allyl, 4-hydroxybutyl, 2-hydroxypropyl, (tetrahydrofuran-2-yl)methyl, or 2-(2-fluorophenyl)ethyl; X represents 2-phenylethyl, (E)-(2-methoxyphenyl)CH~CH—, 4-allyloxyphenyl, 3,4-(methylenedioxy)phenyl, (E)-(4-methoxyphenyl)CH~CH—, 4-fluorophenyl, 3,4-difluorophenyl, or 4-(trifluoromethoxy)phenyl; and R is absent.

In certain embodiments, a compound of the present invention is represented by B and the attendant definitions, wherein Z represents 2-methoxyethyl, 2-hydroxyethyl, 3-methoxypropyl, 3-hydroxypropyl, cyclopropyl, cyclopropylmethyl, ethyl, allyl, 4-hydroxybutyl, 2-hydroxypropyl, (tetrahydrofuran-2-yl)methyl, or 2-(2-fluorophenyl)ethyl; X represents 2-phenylethyl, (E)-(2-methoxyphenyl)CH~CH—, 4-allyloxyphenyl, 3,4-(methylenedioxy)phenyl, (E)-(4-methoxyphenyl)CH~CH—, 4-fluorophenyl, 3,4-difluorophenyl, or 4-(trifluoromethoxy)phenyl; R is absent; and R' represents H.

In assays based on a mammalian anandamide transporter, certain compounds according to structure B have $IC_{50}$ values less than 1 µM, more preferably less than 100 nM, and most preferably less than 10 nM.

In assays based on a mammalian anandamide transporter, certain compounds according to structure B have $EC_{50}$ values less than 1 µM, more preferably less than 100 nM, and most preferably less than 10 nM.

In certain embodiments, a compound of the present invention is represented by C:

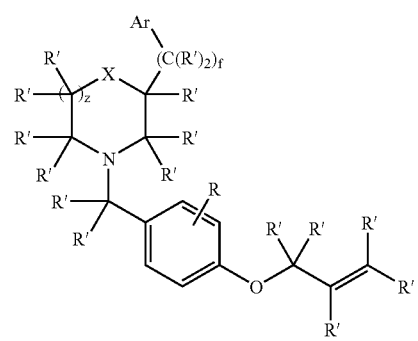

wherein

X represents $C(R')_2$ or O;

Ar represents aryl or heteroaryl;

R is absent or present 1, 2, 3, or 4 times;

R represents independently for each occurrence alkyl, cycloalkyl, alkenyl, alkynyl, aryl, heteroaryl, aralkyl, halogen, heteroaralkyl, hydroxyl, alkoxyl, amino, alkylamino, carboxylate, carboxamide, nitroso, nitro, sulfhydryl, alkylthio, thioalkyl, silyl, alkylsulfonyl, arylsulfonyl, formyl, acyl, acyloxy, acylamino, alkyloxycarbonyl, alkenyloxycarbonyl, aryloxycarbonyl, or —$(CH_2)_n$—$R_{80}$;

R' represents independently for each occurrence H, alkyl, cycloalkyl, aryl, heteroaryl, aralkyl, heteroaralkyl, or —$(CH_2)_n$—$R_{80}$;

$R_{80}$ represents independently for each occurrence cycloalkyl, alkenyl, aryl, heteroaryl, or heterocyclyl;

f represents 1, 2, or 3;

n is an integer selected independently for each occurrence from the range 0 to 8 inclusive;

z represents 0, 1, or 2; provided that when z is 0, X is C(R')$_2$;

the absolute stereochemistry at a stereocenter in a compound represented by C is R, S, or a mixture thereof; and the configuration of an alkenyl moiety in a compound represented by C is E, Z, or a mixture thereof.

In certain embodiments, a compound of the present invention is represented by C and the attendant definitions, wherein R is absent.

In certain embodiments, a compound of the present invention is represented by C and the attendant definitions, wherein R' represents H.

In certain embodiments, a compound of the present invention is represented by C and the attendant definitions, wherein R is absent; and R' represents H.

In assays based on a mammalian anandamide transporter, certain compounds according to structure C have IC$_{50}$ values less than 1 μM, more preferably less than 100 nM, and most preferably less than 10 nM.

In assays based on a mammalian anandamide transporter, certain compounds according to structure C have EC$_{50}$ values less than 1 μM, more preferably less than 100 nM, and most preferably less than 10 nM.

In certain embodiments, a compound of the present invention is represented by D:

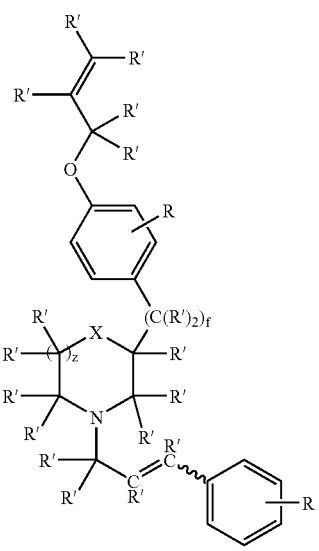

D wherein

X represents C(R')$_2$ or O;

R is independently for each occurrence absent or present 1, 2, 3, or 4 times;

R represents independently for each occurrence alkyl, cycloalkyl, alkenyl, alkynyl, aryl, heteroaryl, aralkyl, halogen, heteroaralkyl, hydroxyl, alkoxyl, amino, alkylamino, carboxylate, carboxamide, nitroso, nitro, sulfhydryl, alkylthio, thioalkyl, silyl, alkylsulfonyl, arylsulfonyl, formyl, acyl, acyloxy, acylamino, alkyloxycarbonyl, alkenyloxycarbonyl, aryloxycarbonyl, or —(CH$_2$)$_n$—R$_{80}$;

R' represents independently for each occurrence H, alkyl, cycloalkyl, aryl, heteroaryl, aralkyl, heteroaralkyl, or —(CH$_2$)$_n$—R$_{80}$;

R$_{80}$ represents independently for each occurrence cycloalkyl, alkenyl, aryl, heteroaryl, or heterocyclyl;

f represents 1, 2, or 3;

n is an integer selected independently for each occurrence from the range 0 to 8 inclusive;

z represents 0, 1, or 2; provided that when z is 0, X is C(R')$_2$;

the absolute stereochemistry at a stereocenter in a compound represented by D is R, S, or a mixture thereof; and the configuration of an alkenyl moiety in a compound represented by D is E, Z, or a mixture thereof.

In certain embodiments, a compound of the present invention is represented by D and the attendant definitions, wherein R is absent.

In certain embodiments, a compound of the present invention is represented by D and the attendant definitions, wherein R' represents H.

In certain embodiments, a compound of the present invention is represented by D and the attendant definitions, wherein R is absent; and R' represents H.

In assays based on a mammalian anandamide transporter, certain compounds according to structure D have IC$_{50}$ values less than 1 μM, more preferably less than 100 nM, and most preferably less than 10 nM.

In assays based on a mammalian anandamide transporter, certain compounds according to structure D have EC$_{50}$ values less than 1 μM, more preferably less than 100 nM, and most preferably less than 10 nM.

In certain embodiments, a compound of the present invention is represented by E:

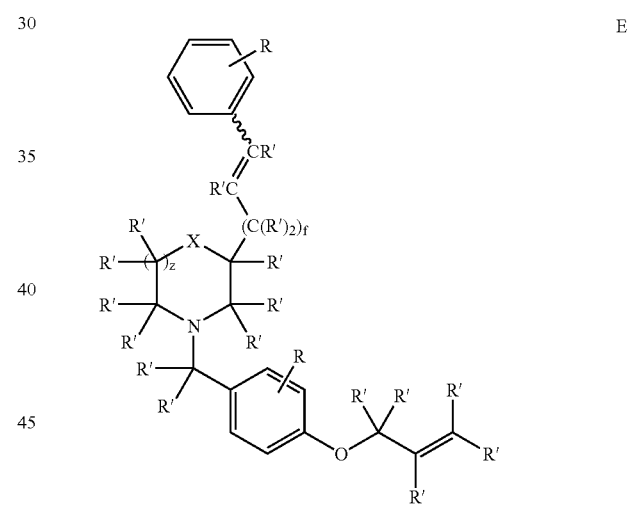

E wherein

X represents C(R')$_2$ or O;

R is independently for each occurrence absent or present 1, 2, 3, or 4 times;

R represents independently for each occurrence alkyl, cycloalkyl, alkenyl, alkynyl, aryl, heteroaryl, aralkyl, halogen, heteroaralkyl, hydroxyl, alkoxyl, amino, alkylamino, carboxylate, carboxamide, nitroso, nitro, sulfhydryl, alkylthio, thioalkyl, silyl, alkylsulfonyl, arylsulfonyl, formyl, acyl, acyloxy, acylamino, alkyloxycarbonyl, alkenyloxycarbonyl, aryloxycarbonyl, or —(CH$_2$)$_n$—R$_{80}$;

R' represents independently for each occurrence H, alkyl, cycloalkyl, aryl, heteroaryl, aralkyl, heteroaralkyl, or —(CH$_2$)$_n$—R$_{80}$;

R$_{80}$ represents independently for each occurrence cycloalkyl, alkenyl, aryl, heteroaryl, or heterocyclyl;

f represents 0 or 1;

n is an integer selected independently for each occurrence from the range 0 to 8 inclusive;

z represents 0, 1, or 2; provided that when z is 0, X is $C(R')_2$;

the absolute stereochemistry at a stereocenter in a compound represented by E is R, S, or a mixture thereof; and the configuration of an alkenyl moiety in a compound represented by E is E, Z, or a mixture thereof.

In certain embodiments, a compound of the present invention is represented by E and the attendant definitions, wherein R is absent.

In certain embodiments, a compound of the present invention is represented by E and the attendant definitions, wherein R' represents H.

In certain embodiments, a compound of the present invention is represented by E and the attendant definitions, wherein R is absent; and R' represents H.

In assays based on a mammalian anandamide transporter, certain compounds according to structure E have $EC_{50}$ values less than 1 µM, more preferably less than 100 nM, and most preferably less than 10 nM.

In assays based on a mammalian anandamide transporter, certain compounds according to structure E have $EC_{50}$ values less than 1 µM, more preferably less than 100 nM, and most preferably less than 10 nM.

In certain embodiments, a compound of the present invention is represented by F:

wherein

X represents $C(R')_2$ or O;

R is independently for each occurrence absent or present 1, 2, 3, or 4 times;

R represents independently for each occurrence alkyl, cycloalkyl, alkenyl, alkynyl, aryl, heteroaryl, aralkyl, halogen, heteroaralkyl, hydroxyl, alkoxyl, amino, alkylamino, carboxylate, carboxamide, nitroso, nitro, sulfhydryl, alkylthio, thioalkyl, silyl, alkylsulfonyl, arylsulfonyl, formyl, acyl, acyloxy, acylamino, alkyloxycarbonyl, alkenyloxycarbonyl, aryloxycarbonyl, or $-(CH_2)_n-R_{80}$;

R' represents independently for each occurrence H, alkyl, cycloalkyl, aryl, heteroaryl, aralkyl, heteroaralkyl, or $-(CH_2)_n-R_{80}$;

$R_{80}$ represents independently for each occurrence cycloalkyl, alkenyl, aryl, heteroaryl, or heterocyclyl;

f represents 1, 2, or 3;

n is an integer selected independently for each occurrence from the range 0 to 8 inclusive;

z represents 0, 1, or 2; provided that when z is 0, X is $C(R')_2$;

the absolute stereochemistry at a stereocenter in a compound represented by F is R, S, or a mixture thereof; and the configuration of an alkenyl moiety in a compound represented by F is E, Z, or a mixture thereof.

In certain embodiments, a compound of the present invention is represented by F and the attendant definitions, wherein R is absent.

In certain embodiments, a compound of the present invention is represented by F and the attendant definitions, wherein R' represents H.

In certain embodiments, a compound of the present invention is represented by F and the attendant definitions, wherein R is absent; and R' represents H.

In assays based on a mammalian anandamide transporter, certain compounds according to structure F have $IC_{50}$ values less than 1 µM, more preferably less than 100 nM, and most preferably less than 10 nM.

In assays based on a mammalian anandamide transporter, certain compounds according to structure F have $EC_{50}$ values less than 1 µM, more preferably less than 100 nM, and most preferably less than 10 nM.

In certain embodiments, a compound of the present invention is represented by G:

wherein

X represents $C(R')_2$ or O;

R is independently for each occurrence absent or present 1, 2, 3, or 4 times;

R represents independently for each occurrence alkyl, cycloalkyl, alkenyl, alkynyl, aryl, heteroaryl, aralkyl, halogen, heteroaralkyl, hydroxyl, alkoxyl, amino, alkylamino, carboxylate, carboxamide, nitroso, nitro, sulfhydryl, alkylthio, thioalkyl, silyl, alkylsulfonyl, arylsulfonyl, formyl, acyl, acyloxy, acylamino, alkyloxycarbonyl, alkenyloxycarbonyl, aryloxycarbonyl, or $-(CH_2)_n-R_{80}$;

R' represents independently for each occurrence H, alkyl, cycloalkyl, aryl, heteroaryl, aralkyl, heteroaralkyl, or $-(CH_2)_n-R_{80}$;

$R_{80}$ represents independently for each occurrence cycloalkyl, alkenyl, aryl, heteroaryl, or heterocyclyl;

f represents 0 or 1;

n is an integer selected independently for each occurrence from the range 0 to 8 inclusive;

z represents 0, 1, or 2; provided that when z is 0, X is $C(R')_2$;

the absolute stereochemistry at a stereocenter in a compound represented by G is R, S, or a mixture thereof; and the configuration of an alkenyl moiety in a compound represented by G is E, Z, or a mixture thereof.

In certain embodiments, a compound of the present invention is represented by G and the attendant definitions, wherein R is absent.

In certain embodiments, a compound of the present invention is represented by G and the attendant definitions, wherein R' represents H.

In certain embodiments, a compound of the present invention is represented by G and the attendant definitions, wherein R is absent; and R' represents H.

In assays based on a mammalian anandamide transporter, certain compounds according to structure G have $IC_{50}$ values less than 1 µM, more preferably less than 100 nM, and most preferably less than 10 nM.

In assays based on a mammalian anandamide transporter, certain compounds according to structure G have $EC_{50}$ values less than 1 µM, more preferably less than 100 nM, and most preferably less than 10 nM.

In certain embodiments, the present invention relates to a compound represented by any of the structures outlined above, wherein said compound is a single stereoisomer.

In certain embodiments, the present invention relates to a formulation, comprising a compound represented by any of the structures outlined above; and a pharmaceutically acceptable excipient.

In certain embodiments, the present invention relates to ligands for a mammalian anandamide transporter, wherein the ligands are represented by any of the structures outlined above, and any of the sets of definitions associated with one of those structures. In certain embodiments, the compounds of the present invention are antagonists or agonists of a mammalian anandamide transporter. In any event, the compounds of the present invention preferably exert their effect on a mammalian anandamide transporter at a concentration less than about 1 micromolar, more preferably at a concentration less than about 100 nanomolar, and most preferably at a concentration less than 10 nanomolar.

The present invention contemplates pharmaceutical formulations comprising a compound of the present invention. In certain embodiments, the pharmaceutical formulations will comprise a compound of the present invention that selectively effects a mammalian anandamide transporter, and thereby has a therapeutic effect on an acute or chronic ailment, disease or malady that is at least in part due to biochemical or physiological processes associated with a mammalian anandamide transporter. For example, the Background of the Invention (see above) teaches examples of acute or chronic ailments, diseases or maladies that are caused or exacerbated by biochemical or physiological processes associated with a mammalian anandamide transporter. One of ordinary skill in the art will be able to accumulate, by reference to the scientific literature, a more comprehensive list of acute or chronic ailments, diseases or maladies that are caused or exacerbated by biochemical or physiological processes associated with a mammalian anandamide transporter. The present invention contemplates that pharmaceutical formulations comprising a compound of the present invention will be of medicinal value against the aforementioned acute or chronic ailments, diseases or maladies.

In certain embodiments, the present invention relates to methods of treating a mammal suffering from asthma, neuropathic pain, persistent pain, inflammatory pain, hyperactivity, hypertension, brain ischemia, Parkinson's disease, spasticity, Tourette's syndrome, schizophrenia, hemorrhagic shock, septic shock, cardiac shock, migrane, Horton's headache, multiple sclerosis, anorexia, AIDS wasting syndrome, organ rejection, autoimmune diseases, allergy, arthritis, Crohn's disease, malignant gliomas, neurodegenerative diseases, Huntington's chorea, glaucoma, nausea, anxiety, psychosis, attention deficit hyperactivity disorder, premature ejaculation, or stroke, comprising administering to said mammal a therapeutically effective amount of a compound of the present invention.

The methods of treating can be prophylactic, therapeutic, or curative. When the methods of treating are practiced prior to an individual showing any clinical sign or symptom of a disease or disorder, they are considered prophylactic. Prophylactic treating can be practiced, for example, on individuals suspected of having a disease or disorder, or on individuals suspected of being at high risk of developing a disease or disorder. In embodiments, prophylactic methods reduce or eliminate the risk of developing a disease or disorder characterized by undesirable vasoconstriction. In embodiments, prophylactic methods reduce or eliminate the risk of developing a disease or disorder characterized by undesirable inflammation. In embodiments, prophylactic methods reduce or eliminate the risk of developing a disease or disorder characterized by undesirable pain. In embodiments, prophylactic methods reduce or eliminate the risk of developing a disease or disorder characterized by undesirable organ dysfunction.

When the methods of treating are practiced on an individual already showing at least one clinical sign or symptom of a disease or disorder, the methods can be therapeutic or curative. Therapeutic methods are those methods that result in a detectable change in at least one symptom of the disease or disorder. Preferably, the detectable change is an improvement in the symptom. In embodiments, therapeutic methods reduce or eliminate undesirable vasoconstriction. In embodiments, therapeutic methods reduce or eliminate undesirable inflammation. In embodiments, therapeutic methods reduce or eliminate undesirable pain. In embodiments, therapeutic methods reduce or eliminate undesirable organ dysfunction.

Curative methods are those therapeutic methods that result in elimination of at least one symptom of a disease or disorder. Preferably, curative methods eliminate the cause of the disease or disorder. In embodiments, curative methods eliminate undesirable vasoconstriction. In embodiments, curative methods eliminate undesirable inflammation. In embodiments, curative methods eliminate undesirable pain. In embodiments, curative methods eliminate undesirable organ dysfunction.

In embodiments, the methods of treating include administering a compound of the present invention to an individual in an amount sufficient to bring about the intended result. For example, in embodiments, a compound of the present invention is administered in an amount sufficient to modulate vascular tone; in an amount sufficient to modulate inflammation; in an amount sufficient to modulate sensory nerve activity; in an amount sufficient to achieve analgesia; and/or in an amount sufficient to modulate organ function. In embodiments, a compound of the present invention is administered to an individual in an amount sufficient to achieve a detectable change in the disease, disorder, or symptom being treated. The change can be a change throughout the body of the treated individual or at a specific site within or on the surface of the treated individual. Thus, the methods of treating include systemic treating as well as localized treating.

The methods of treating can include a single administration to an individual, or can include multiple administrations. Treatment and dosing regimens can be designed and implemented in accordance with those that are well-known and widely practiced in the art. It is contemplated that each regimen will be tailored to the individual to be treated and the disease(s), disorder(s), and/or symptom(s) involved. However, such individual tailoring is well within the skill of those in the art and does not involve undue or excessive experimentation.

The present invention also provides kits containing a compound of the present invention that affects the activity of a mammalian anandamide transporter. In embodiments, a compound of the present invention is provided in the kit as the sole component of the kit. In embodiments, it is present as part of a composition. In embodiments, it is provided in combination with other compounds, solutions, or devices necessary or desirable for use of the compounds and/or compositions contained therein. Thus, the kits of the invention can contain all the necessary compounds, solutions, and equipment for administration of the compounds and compositions contained therein to an individual, or the kits can be designed for in vitro use of a compound of the present invention.

Biochemical Activity at Cellular Receptors, and Assays to Detect that Activity

Assaying processes are well known in the art in which a reagent is added to a sample, and measurements of the sample and reagent are made to identify sample attributes stimulated by the reagent. For example, one such assay process concerns determining in a chromogenic assay the amount of an enzyme present in a biological sample or solution. Such assays are based on the development of a colored product in the reaction solution. The reaction develops as the enzyme catalyzes the conversion of a colorless chromogenic substrate to a colored product.

Another assay useful in the present invention concerns determining the ability of a ligand to bind to a biological receptor utilizing a technique well known in the art referred to as a radioligand binding assay. This assay accurately determines the specific binding of a radioligand to a targeted receptor through the delineation of its total and nonspecific binding components. Total binding is defined as the amount of radioligand that remains following the rapid separation of the radioligand bound in a receptor preparation (cell homogenates or recombinate receptors) from that which is unbound. The nonspecific binding component is defined as the amount of radioligand that remains following separation of the reaction mixture consisting of receptor, radioligand and an excess of unlabeled ligand. Under this condition, the only radioligand that remains represents that which is bound to components other that receptor. The specific radioligand bound is determined by subtracting the nonspecific from total radioactivity bound. For a specific example of radioligand binding assay for µ-opioid receptor, see Wang, J. B. et al. *FEBS Letters* 1994, 338, 217.

Assays useful in the present invention concern determining the activity of receptors the activation of which initiates subsequent intracellular events in which intracellular stores of calcium ions are released for use as a second messenger. Activation of some G-protein-coupled receptors stimulates the formation of inositol triphosphate (IP3, a G-protein-coupled receptor second messenger) through phospholipase C-mediated hydrolysis of phosphatidylinositol, Berridge and Irvine (1984). Nature 312:315–21. IP3 in turn stimulates the release of intracellular calcium ion stores.

A change in cytoplasmic calcium ion levels caused by release of calcium ions from intracellular stores is used to determine G-protein-coupled receptor function. This is another type of indirect assay. Among G-protein-coupled receptors are muscarinic acetylcholine receptors (mAChR), adrenergic receptors, sigma receptors, serotonin receptors, dopamine receptors, angiotensin receptors, adenosine receptors, bradykinin receptors, metabotropic excitatory amino acid receptors and the like. Cells expressing such G-protein-coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores. Another type of indirect assay involves determining the activity of receptors which, when activated, result in a change in the level of intracellular cyclic nucleotides, e.g., cAMP, cGMP. For example, activation of some dopamine, serotonin, metabotropic glutamate receptors and muscarinic acetylcholine receptors results in a decrease in the cAMP or cGMP levels of the cytoplasm.

Furthermore, there are cyclic nucleotide-gated ion channels, e.g., rod photoreceptor cell channels and olfactory neuron channels [see, Altenhofen, W. et al. (1991) Proc. Natl. Acad. Sci U.S.A. 88:9868–9872 and Dhallan et al. (1990) Nature 347:184–187] that are permeable to cations upon activation by binding of cAMP or cGMP. A change in cytoplasmic ion levels caused by a change in the amount of cyclic nucleotide activation of photo-receptor or olfactory neuron channels is used to determine function of receptors that cause a change in cAMP or cGMP levels when activated. In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. Cell for this type of assay can be made by co-transfection of a host cell with DNA encoding a cyclic nucleotide-gated ion channel and a DNA encoding a receptor (e.g., certain metabotropic glutamate receptors, muscarinic acetylcholine receptors, dopamine receptors, serotonin receptors and the like, which, when activated, causes a change in cyclic nucleotide levels in the cytoplasm.

Any cell expressing a receptor protein which is capable, upon activation, of directly increasing the intracellular concentration of calcium, such as by opening gated calcium channels, or indirectly affecting the concentration of intracellular calcium as by causing initiation of a reaction which utilizes $Ca^{2+}$ as a second messenger (e.g., G-protein-coupled receptors), may form the basis of an assay. Cells endogenously expressing such receptors or ion channels and cells which may be transfected with a suitable vector encoding one or more such cell surface proteins are known to those of skill in the art or may be identified by those of skill in the art. Although essentially any cell which expresses endogenous ion channel and/or receptor activity may be used, it is preferred to use cells transformed or transfected with heterologous DNAs encoding such ion channels and/or receptors so as to express predominantly a single type of ion channel or receptor. Many cells that may be genetically engineered to express a heterologous cell surface protein are known. Such cells include, but are not limited to, baby hamster kidney (BHK) cells (ATCC No. CCL10), mouse L cells (ATCC No. CCLI.3), DG44 cells [see, Chasin (1986) Cell. Molec. Genet. 12:555] human embryonic kidney (HEK) cells (ATCC No. CRL1573), Chinese hamster ovary (CHO) cells (ATCC Nos. CRL9618, CCL61, CRL9096), PC12 cells (ATCC No. CRL1721) and COS-7 cells (ATCC No. CRL1651). Preferred cells for heterologous cell surface protein expression are those that can be readily and efficiently transfected. Preferred cells include HEK 293 cells, such as those described in U.S. Pat. No. 5,024,939.

Any compound which is known to activate ion channels or receptors of interest may be used to initiate an assay. Choosing an appropriate ion channel- or receptor-activating reagent depending on the ion channel or receptor of interest is within the skill of the art. Direct depolarization of the cell membrane to determine calcium channel activity may be accomplished by adding a potassium salt solution having a concentration of potassium ions such that the final concentration of potassium ions in the cell-containing well is in the range of about 50–150 mM (e.g., 50 mM KCl). With respect to ligand-gated receptors and ligand-gated ion channels, ligands are known which have affinity for and activate such receptors. For example, nicotinic acetyloholine receptors are known to be activated by nicotine or acetylcholine; similarly, muscarinic and acetylcholine receptors may be activated by addition of muscarine or carbamylcholine.

Agonist assays may be carried out on cells known to possess ion channels and/or receptors to determine what effect, if any, a compound has on activation or potentiation of ion channels or receptors of interest. Agonist assays also may be carried out using a reagent known to possess ion channel- or receptor-activating capacity to determine whether a cell expresses the respective functional ion channel or receptor of interest.

Contacting a functional receptor or ion channel with agonist typically activates a transient reaction; and prolonged exposure to an agonist may desensitize the receptor or ion channel to subsequent activation. Thus, in general, assays for determining ion channel or receptor function should be initiated by addition of agonist (i.e., in a reagent solution used to initiate the reaction). The potency of a compound having agonist activity is determined by the detected change in some observable in the cells (typically an increase, although activation of certain receptors causes a decrease) as compared to the level of the observable in either the same cell, or substantially identical cell, which is treated substantially identically except that reagent lacking the agonist (i.e., control) is added to the well. Where an agonist assay is performed to test whether or not a cell expresses the functional receptor or ion channel of interest, known agonist is added to test-cell-containing wells and to wells containing control cells (substantially identical cell that lacks the specific receptors or ion channels) and the levels of observable are compared. Depending on the assay, cells lacking the ion channel and/or receptor of interest should exhibit substantially no increase in observable in response to the known agonist. A substantially identical cell may be derived from the same cells from which recombinant cells are prepared but which have not been modified by introduction of heterologous DNA. Alternatively, it may be a cell in which the specific receptors or ion channels are removed. Any statistically or otherwise significant difference in the level of observable indicates that the test compound has in some manner altered the activity of the specific receptor or ion channel or that the test cell possesses the specific functional receptor or ion channel.

In an example of drug screening assays for identifying compounds which have the ability to modulate ion channels or receptors of interest, individual wells (or duplicate wells, etc.) contain a distinct cell type, or distinct recombinant cell line expressing a homogeneous population of a receptor or ion channel of interest, so that the compound having unidentified activity may be screened to determine whether it possesses modulatory activity with respect to one or more of a variety of functional ion channels or receptors. It is also contemplated that each of the individual wells may contain the same cell type so that multiple compounds (obtained from different reagent sources in the apparatus or contained within different wells) can be screened and compared for modulating activity with respect to one particular receptor or ion channel type.

Antagonist assays, including drug screening assays, may be carried out by incubating cells having functional ion channels and/or receptors in the presence and absence of one or more compounds, added to the solution bathing the cells in the respective wells of the microtiter plate for an amount of time sufficient (to the extent that the compound has affinity for the ion channel and/or receptor of interest) for the compound(s) to bind to the receptors and/or ion channels, then activating the ion channels or receptors by addition of known agonist, and measuring the level of observable in the cells as compared to the level of observable in either the same cell, or substantially identical cell, in the absence of the putative antagonist.

The assays are thus useful for rapidly screening compounds to identify those that modulate any receptor or ion channel in a cell. In particular, assays can be used to test functional ligand-receptor or ligand-ion channel interactions for cell receptors including ligand-gated ion channels, voltage-gated ion channels, G-protein-coupled receptors and growth factor receptors.

Those of ordinary skill in the art will recognize that assays may encompass measuring a detectable change of a solution as a consequence of a cellular event which allows a compound, capable of differential characteristics, to change its characteristics in response to the cellular event. By selecting a particular compound which is capable of differential characteristics upon the occurrence of a cellular event, various assays may be performed. For example, assays for determining the capacity of a compound to induce cell injury or cell death may be carried out by loading the cells with a pH-sensitive fluorescent indicator such as BCECF (Molecular Probes, Inc., Eugene, Oreg. 97402, Catalog #B1150) and measuring cell injury or cell death as a function of changing fluorescence over time.

In a further example of useful assays, the function of receptors whose activation results in a change in the cyclic nucleotide levels of the cytoplasm may be directly determined in assays of cells that express such receptors and that have been injected with a fluorescent compound that changes fluorescence upon binding cAMP. The fluorescent compound comprises cAMP-dependent-protein kinase in which the catalytic and regulatory subunits are each labelled with a different fluorescent-dye [Adams et al. (1991) Nature 349:694–697]. When cAMP binds to the regulatory subunits, the fluorescence emission spectrum changes; this change can be used as an indication of a change in cAMP concentration.

The function of certain neurotransmitter transporters which are present at the synaptic cleft at the junction between two neurons may be determined by the development of fluorescence in the cytoplasm of such neurons when conjugates of an amine acid and fluorescent indicator (wherein the fluorescent indicator of the conjugate is an acetoxymethyl ester derivative e.g., 5-(aminoacetamido) fluorescein; Molecular Probes, Catalog #A1363) are transported by the neurotransmitter transporter into the cytoplasm of the cell where the ester group is cleaved by esterase activity and the conjugate becomes fluorescent.

In practicing an assay of this type, a reporter gene construct is inserted into an eukaryotic cell to produce a recombinant cell which has present on its surface a cell surface protein of a specific type. The cell surface receptor may be endogenously expressed or it may be expressed from a heterologous gene that has been introduced into the cell. Methods for introducing heterologous DNA into eukaryotic cells are-well known in the art and any such method may be used. In addition, DNA encoding various cell surface proteins is known to those of skill in the art or it may be cloned by any method known to those of skill in the art.

The recombinant cell is contacted with a test compound and the level of reporter gene expression is measured. The contacting may be effected in any vehicle and the testing may be by any means using any protocols, such as serial dilution, for assessing specific molecular interactions known to those of skill in the art. After contacting the recombinant cell for a sufficient time to effect any interactions, the level of gene expression is measured. The amount of time to effect such interactions may be empirically determined, such as by running a time course and measuring the level of transcription as a function of time. The amount of transcription may be measured using any method known to those of skill in the art to be suitable. For example, specific mRNA expression may be detected using Northern blots or specific protein product may be identified by a characteristic stain. The amount of transcription is then compared to the amount of transcription in either the same cell in the absence of the test. compound or it may be compared with the amount of transcription in a substantially identical cell that lacks the specific receptors. A substantially identical cell may be derived from the same cells from which the recombinant cell was prepared but which had not been modified by introduction of heterologous DNA. Alternatively, it may be a cell in which the specific receptors are removed. Any statistically or otherwise significant difference in the amount of transcription indicates that the test compound has in some manner altered the activity of the specific receptor.

If the test compound does not appear to enhance, activate or induce the activity of the cell surface protein, the assay may be repeated and modified by the introduction of a step in which the recombinant cell is first tested for the ability of a known agonist or activator of the specific receptor to activate transcription if the transcription is induced, the test compound is then assayed for its ability to inhibit, block or otherwise affect the activity of the agonist.

The transcription based assay is useful for identifying compounds that interact with any cell surface protein whose activity ultimately alters gene expression. In particular, the assays can be used to test functional ligand-receptor or ligand-ion channel interactions for a number of categories of cell surface-localized receptors, including: ligand-gated ion channels and voltage-gated ion channels, and G protein-coupled receptors.

Any transfectable cell that can express the desired cell surface protein in a manner such the protein functions to intracellularly transduce an extracellular signal may be used. The cells may be selected such that they endogenously express the cell surface protein or may be genetically engineered to do so. Many such cells are known to those of skill in the art. Such cells include, but are not limited to Ltk<–> cells, PC12 cells and COS-7 cells.

The preparation of cells which express a receptor or ion channel and a reporter gene expression construct, and which are useful for testing compounds to assess their activities, is exemplified in the Examples provided herewith by reference to mammalian Ltk<–> and COS-7 cell lines, which express the Type I human muscarinic (HM1) receptor and which are transformed with either a c-fos promoter-CAT reporter gene expression construct or a c-fos promoter-luciferase reporter gene expression construct.

Any cell surface protein that is known to those of skill in the art or that may be identified by those of skill in the art may be used in the assay. The cell surface protein may be endogenously expressed on the selected cell or it may be expressed from cloned DNA. Exemplary cell surface proteins include, but are not limited to, cell surface receptors and ion channels. Cell surface receptors include, but are not limited to, muscarinic receptors (e.g., human M2 (GenBank accession #M16404); rat M3 (GenBank accession #M16407); human M4 (GenBank accession #M16405); human M5 (Bonner et al. (1988) Neuron 1:403–410); and the like); neuronal nicotinic acetylcholine receptors (e.g., the alpha 2, alpha 3 and beta 2 subtypes disclosed in U.S. Ser. No. 504,455 (filed Apr. 3, 1990), hereby expressly incorporated by reference herein in its entirety); the rat alpha 2 subunit (Wada et al. (1988) Science 240:330–334); the rat alpha 3 subunit (Boulter et al. (1986) Nature 319:368–374); the rat alpha 4 subunit (Goldman et al. (1987) cell 48:965–973); the rat alpha 5 subunit (Boulter et al. (1990) J. Biol. Chem. 265:4472–4482); the rat beta 2 subunit (Deneris et al. (1988) Neuron 1:45–54); the rat beta 3 subunit (Deneris et al. (1989) J. Biol. Chem. 264: 6268–6272); the rat beta 4 subunit (Duvoisin et al. (1989) Neuron 3:487–496); combinations of the rat alpha subunits, beta subunits and alpha and beta subunits; GABA receptors (e.g., the bovine alpha 1 and beta 1 subunits (Schofield et al. (1987) Nature 328:221–227); the bovine alpha 2 and alpha 3 subunits (Levitan et al. (1988) Nature 335:76–79); the gamma -subunit (Pritchett et al. (1989) Nature 338:582–585); the beta 2 and beta 3 subunits (Ymer et alo (1989) EMBO J. 8:1665–1670); the delta subunit (Shivers, B. D. (1989) Neuron 3:327–337); and the like); glutamate receptors (e.g., receptor isolated from rat brain (Hollmann et al. (1989) Nature 342:643–648); and the like); adrenergic receptors (e.g., human beta 1 (Frielle et al. (1987) Proc. Natl. Acad. Sci. 84.:7920–7924); human alpha 2 (Kobilka et al. (1987) Science 238:650–656); hamster beta 2 (Dixon et al. (1986) Nature 321:75–79); and the like); dopamine receptors (e.g., human D2 (Stormann et al. (1990) Molec. Pharm.37:1–6); rat (Bunzow et al. (1988) Nature 336: 783–787); and the like); NGF receptors (e.g., human NGF receptors (Johnson et al. (1986) Cell 47:545–554); and the like); serotonin receptors (e.g., human 5HT1a (Kobilka et al. (1987) Nature 329:75–79); rat 5HT2 (Julius et al. (1990) PNAS 87:928–932); rat 5HT1c (Julius et al. (1988) Science 241:558–564); and the like).

Reporter gene constructs are prepared by operatively linking a reporter gene with at least one transcriptional regulatory element. If only one transcriptional regulatory element is included it must be a regulatable promoter. At least one of the selected transcriptional regulatory elements must be indirectly or directly regulated by the activity of the selected cell-surface receptor whereby activity of the receptor can be monitored via transcription of the reporter genes.

The construct may contain additional transcriptional regulatory elements, such as a FIRE sequence, or other sequence, that is not necessarily regulated by the cell surface protein, but is selected for its ability to reduce background level transcription or to amplify the transduced signal and to thereby increase the sensitivity and reliability of the assay.

Many reporter genes and transcriptional regulatory elements are known to those of skill in the art and others may be identified or synthesized by methods known to those of skill in the art.

A reporter gene includes any gene that expresses a detectable gene product, which may be RNA or protein. Preferred reporter genes are those that are readily detectable. The reporter gene may also be included in the construct in the form of a fusion gene with a gene that includes desired transcriptional regulatory sequences or exhibits other desirable properties.

Examples of reporter genes include, but are not limited to CAT (chloramphenicol acetyl transferase) (Alton and Vapnek (1979), Nature 282: 864–869) luciferase, and other enzyme detection systems, such as beta-galactosidase; firefly luciferase (deWet et al. (1987), Mol. Cell. Biol. 7:725–737); bacterial luciferase (Engebrecht and Silverman (1984), PNAS 1: 4154–4158; Baldwin et al. (1984), Biochemistry 23: 3663–3667); alkaline phosphatase (Toh et al. (1989) Eur. J. Biochem. 182: 231–238, Hall et al. (1983) J. Mol. Appl. Gen. 2: 101).

Transcriptional control elements include, but are not limited to, promoters, enhancers, and repressor and activator binding sites. Suitable transcriptional regulatory elements may be derived from the transcriptional regulatory regions of genes whose expression is rapidly induced, generally within minutes, of contact between the cell surface protein and the effector protein that modulates the activity of the cell surface protein. Examples of such genes include, but are not limited to, the immediate early genes (see, Sheng et al. (1990) Neuron 4: 477–485), such as c-fos. Immediate early genes are genes that are rapidly induced upon binding of a ligand to a cell surface protein. The transcriptional control elements that are preferred for use in the gene constructs include transcriptional control elements from immediate early genes, elements derived from other genes that exhibit some or all of the characteristics of the immediate early genes, or synthetic elements that are constructed such that genes in operative linkage therewith exhibit such characteristics. The characteristics of preferred genes from which the transcriptional control elements are derived include, but are not limited to, low or undetectable expression in quiescent cells, rapid induction at the transcriptional level within minutes of extracellular simulation, induction that is transient and independent of new protein synthesis, subsequent shut-off of transcription requires new protein synthesis, and mRNAs transcribed from these genes have a short half-life. It is not necessary for all of these properties to be present.

Pharmaceutical Compositions

In another aspect, the present invention provides pharmaceutically acceptable compositions which comprise a therapeutically effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing acid (e.g., lubricant, talc magnesium, calcium stearate, zinc stearate, or stearic acid) or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthate, mesylate, glucoheptonate, lactobionate, and laurylsulphonate salts and the like. (See, for example, Berge et al. (1977) "Pharmaceutical Salts", J. Pharm. Sci. 66:1–19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 0.1 per cent to about ninety-nine percent of active ingredient, preferably from about 5 per cent to about 70 per cent, most preferably from about 10 per cent to about 30 per cent.

In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres.

They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient, when used for the indicated desired effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. However, the preferred dosing is daily.

While it is possible for a compound of the present invention to be administered alone, it is preferable to administer the compound as a pharmaceutical formulation (composition).

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or oral cavity; or (4) intravaginally or intravectally, for example, as a pessary, cream or foam; (5) sublingually; (6) ocularly; (7) transdermally; or (8) nasally.

The compounds according to the invention may be formulated for administration in any convenient way for use in human or veterinary medicine, by analogy with other pharmaceuticals.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W. H. Freedman and CO., San Francisco, U.S.A., 1969 or "Livestock Feeds and Feeding" O and B books, Corvallis, Oreg., U.S.A., 1977).

Combinatorial Libraries

The subject compounds readily lend themselves to the creation of combinatorial libraries for the screening of pharmaceutical, agrochemical or other biological or medically-related activity or material-related qualities. See FIGS. 1 and 2. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library can be created at a variety of different levels. For instance, the substrate aryl groups used in a combinatorial approach can be diverse in terms of the core aryl moiety, e.g., a variegation in terms of the ring structure, and/or can be varied with respect to the other substituents.

A variety of techniques are available in the art for generating combinatorial libraries of small organic molecules. See, for example, Blondelle et al. (1995) Trends Anal. Chem. 14:83; the Affymax U.S. Pat. Nos. 5,359,115 and 5,362,899: the Ellman U.S. Pat. No. 5,288,514: the Still et al. PCT publication WO 94/08051; Chen et al. (1994) JACS 116: 2661: Kerr et al. (1993) JACS 115:252; PCT publications WO92/10092, WO93/09668 and WO91/07087; and the Lemer et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

A. Direct Characterization

A growing trend in the field of combinatorial chemistry is to exploit the sensitivity of techniques such as mass spectrometry (MS), e.g., which can be used to characterize sub-femtomolar amounts of a compound, and to directly determined the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

B) Multipin Synthesis

The libraries of the subject method can take the multipin library format. Briefly, Geysen and co-workers (Geysen et al. (1984) PNAS 81:3998–4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also be appended to the pins so that the compounds may be cleaved from the supports after synthesis for assessment of purity and further evaluation (c.f., Bray et al. (1990) Tetrahedron Lett 31:5811–5814; Valerio et al. (1991) Anal Biochem 197:168–177; Bray et al. (1991)Tetrahedron Lett 32:6163–6166).

C) Divide-Couple-Recombine

In yet another embodiment, a variegated library of compounds can be provided on a set of beads utilizing the strategy of divide-couple-recombine (see, e.g., Houghten (1985) PNAS 82:5131–5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) PNAS 82:5131–5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D) Combinatorial Libraries by Light-Directed Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) Annu Rep Med Chem 26:271–280; Fodor, S. P. A. (1991) Science 251:767; Pirrung et al. (1992) U.S. Pat. No. 5,143,854; Jacobs et al. (1994) Trends Biotechnol 12:19–26). The spatial resolution of photolithography affords miniaturization. This technique can be carried out through the use of protection/deprotection reactions with photolabile protecting groups.

The key points of this technology are illustrated in Gallop et al. (1994) J Med Chem 37:1233–1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E) Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging with Sequenceable Bio-Oligomers

The principle of using oligonucleotides to encode combinatorial synthetic libraries was described in 1992 (Brenner et al. (1992) PNAS 89:5381–5383), and an example of such a library appeared the following year (Needles et al. (1993) *PNAS* 90:10700–10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of a library member for assaying.

Peptides have also been employed as tagging molecules for combinatorial libraries. Two exemplary approaches are described in the art, both of which employ branched linkers to solid phase upon which coding and ligand strands are alternately elaborated. In the first approach (Kerr JM et al. (1993) *J Am Chem Soc* 115:2529–2531), orthogonality in synthesis is achieved by employing acid-labile protection for the coding strand and base-labile protection for the compound strand.

In an alternative approach (Nikolaiev et al. (1993) *Pept Res* 6:161–170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) *Tetrahedron Lett* 32:3891–3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

2) Non-sequenceable Tagging: Binary Encoding

An alternative form of encoding the test compound library employs a set of non-sequencable electrophoric tagging molecules that are used as a binary code (Ohlmeyer et al. (1993) *PNAS* 90:10922–10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) *J Org Chem* 59:4723–4724). This orthogonal attachment strategy permits the selective detachment of library members for assays in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) *PNAS* 92:6027–6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

EXEMPLIFICATION

The invention now being generally described, it will be more readily understood by reference to the following examples, which are included merely for purposes of illustration of certain aspects and embodiments of the present invention, and are not intended to limit the invention.

Example 1

Solid-Phase Synthesis of N-(4-Allyloxybenzyl)-N-(2-methoxyethyl)-N-(3-phenyl-allyl)amine (4)

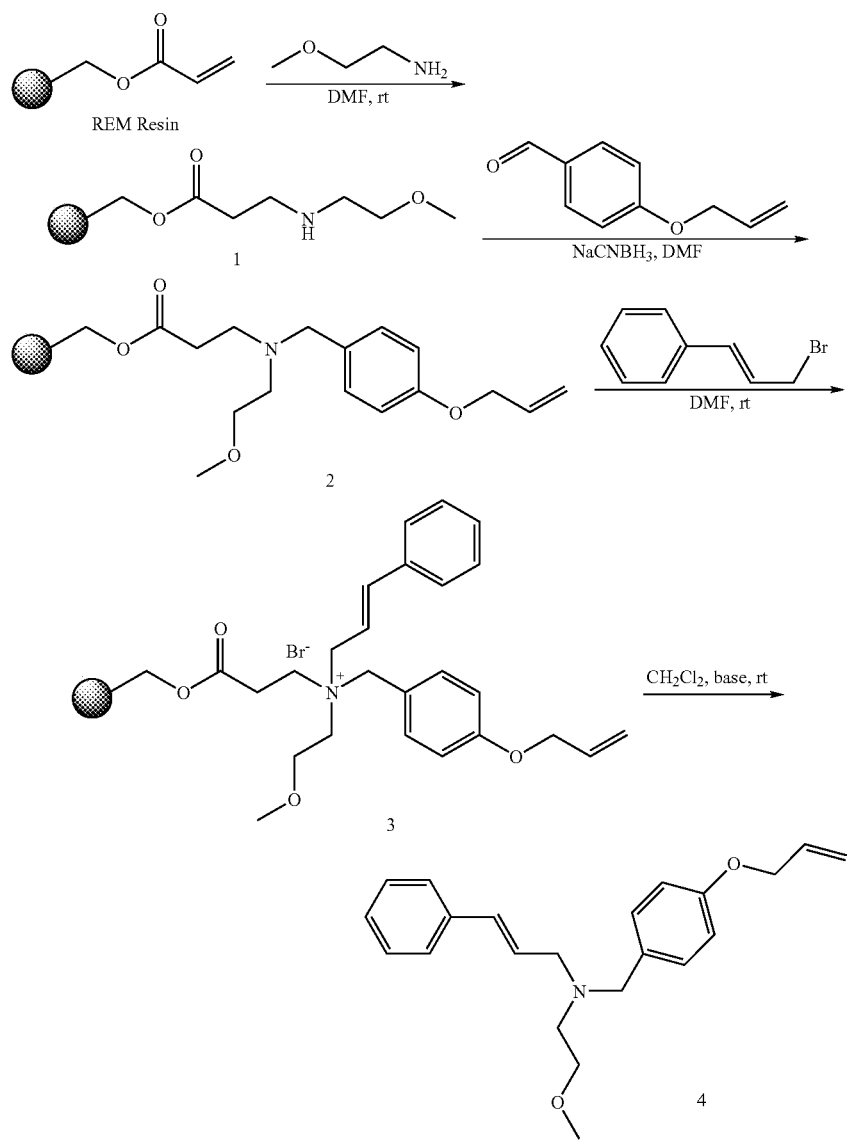

To REM resin (0.10 g, 1.06 mmol/g) in a 3 mL polypropylene filtration tube with polyethylene frit was added DMF (1 mL), followed by 2-methoxyethylamine (92 μL, 1.06 mmol). The mixture was shaken at room temperature for 24 hours. The resulting resin (1) was washed with DMF (3×1 mL), MeOH (4×1 mL), and CH$_2$Cl$_2$ (4×1 mL), then dried in vacuo. To the resin (1) was added 4-allyloxybenzaldehyde (153 μL, 1.06 mmol) in DMF (1 mL), and NaCNBH$_3$ (133 mg, 2.12 mmol), followed by acetic acid (10 μL). After shaking at room temperature overnight, the resulting resin (2) was washed with DMF (3×1 mL), MeOH (4×1 mL), and CH$_2$Cl$_2$ (4×1 mL), then dried in vacuo. The dry resin (2) was suspended in a solution of cinnamyl bromide (209 mg, 1.06 mmol) in DMF (1 mL), and agitated at room temperature for 24 hours to give resin (3). Filtration, was followed by rinsing with DMF (3×1 mL), MeOH (4×1 mL), and CH$_2$Cl$_2$ (4×1 mL), and the resin was then dried in vacuo. To the dry resin (3) was added polyamine resin (0.10 g, 2.43 mmol/g) and CH$_2$Cl$_2$ (2 mL). The mixture was agitated at room temperature for 24 hours, then filtered and washed with CH$_2$Cl$_2$ (2×1.5 mL). The filtrates were collected and evaporated to yield 4 (15 mg, 42% yield, >95% purity by HPLC, LRMS m/z 338) as a colorless oil.

Example 2

Solid-Phase Synthesis of Tertiary Amines 5–12

Individual compounds 5, 6, 7, 8, 9, 10, 11, and 12 were prepared using the general procedure described in Example 1 for the synthesis of 4. The overall yield of each of these compounds was 35% to 45%, and the purity of each compound was >95%.

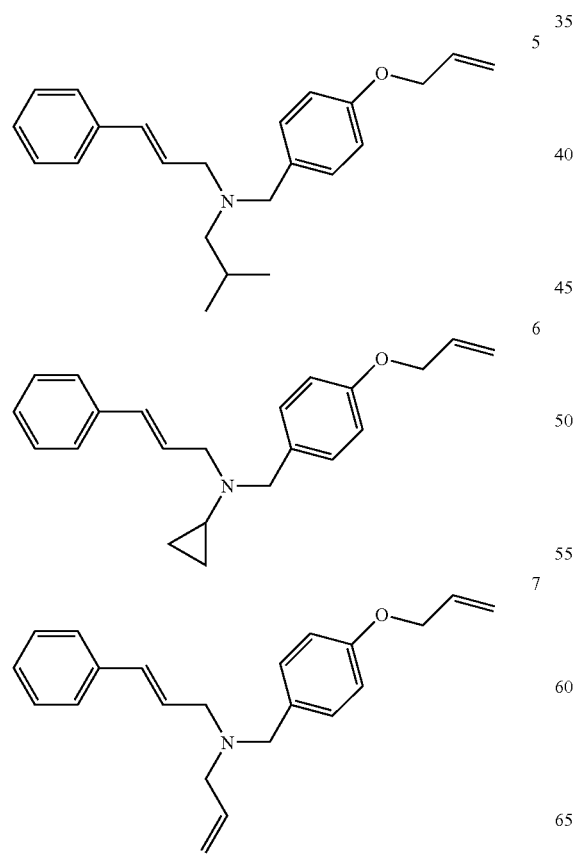

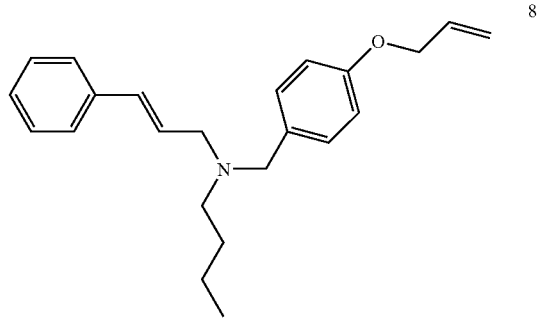

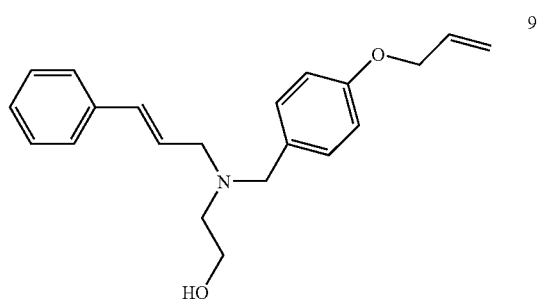

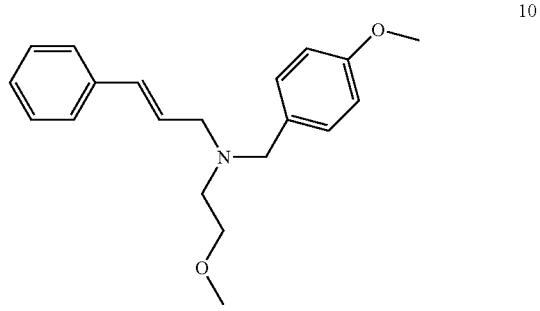

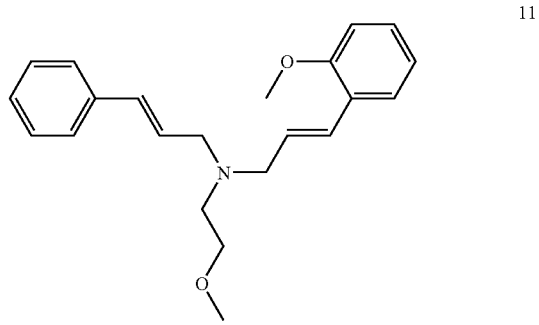

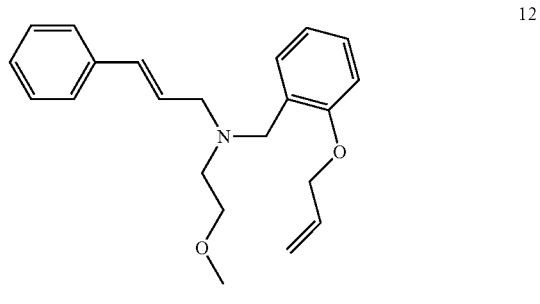

Example 3

Solid-Phase Synthesis of a Combinatorial Library of Anandamide Transporter Inhibitors Comprising a Cinnamyl Moiety (See FIG. 1)

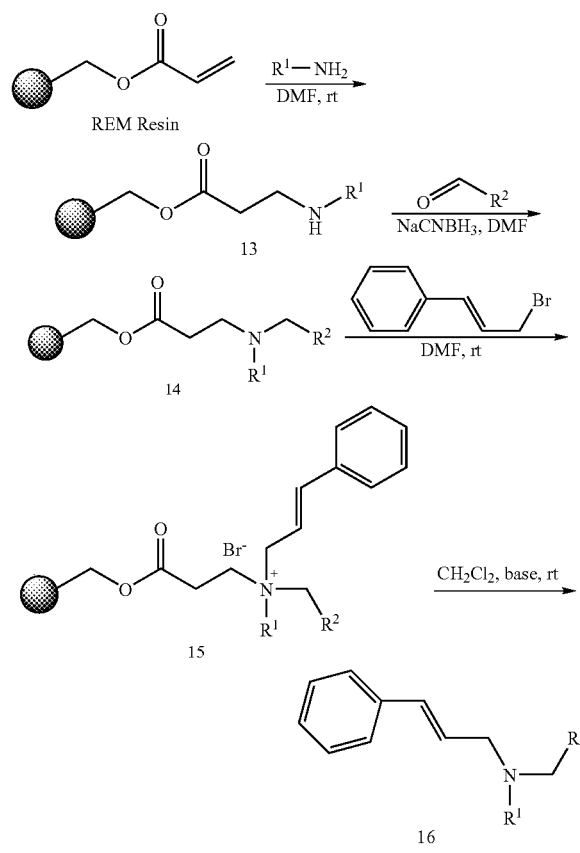

REM resin (1.06 mmol/g) was distributed into twelve 12 mL filtration tubes (0.80 g/tube, 0.848 mmol) followed by dispensing DMF at 8 mL/tube. Twelve amines were respectively added into twelve reaction tubes at 8.48 mmol/tube. After shaking at room temperature for 24 hours, the resulting resins (13) were washed with DMF (3×8 mL), MeOH (4×8 mL), and $CH_2Cl_2$ (4×8 mL), the n dried in vacuo. Twelve resins were respectively dispensed into a 96-well reaction block from column 1 to column 12 at 0.10 g (0.106 mmol)/well. Eight aldehydes (A to H) in DMF were respectively dispensed into eight rows, from row A to row H at 1.0 mL/well (containing 1.06 mmol aldehyde), then $NaCNBH_3$ was dispensed into 96 wells at 133 mg/well followed by adding acetic acid at 10 µL/well. After shaking at room temperature overnight, the reaction mixtures were filtered, and the resins were washed with DMF (3×1 mL/well), MeOH (4×1 mL/well), and $CH_2Cl_2$ (4×1 mL/well), then dried in vacuo. Cinnamyl bromide (20 g, 102 mmol) in DMF (96 mL) was dispensed into 96 wells at 1.0 mL/well. After shaking at room temperature for 24 hours, the reaction mixtures were filtered and the resins were washed with DMF (3×1 mL/well), MeOH (4×1 mL/well), and $CH_2Cl_2$ (4×1 mL/well), then dried in vacuo. Polyamine resin (2.43 mmol/g) was dispensed into 96 wells at 0.10 g/well followed by dispensing $CH_2Cl_2$ at 2 mL/well. The mixtures were agitated at room temperature for 24 hours, then filtered and washed with $CH_2Cl_2$ (2×1.5 mL/well). The filtrates were collected and evaporated to yield 96 final compounds, represented by general structure 16, which were submitted to HPLC and mass spectra analyses.

The molecular ion $(M+H^+)$ observed in LRMS experiments and the yield obtained for each of the members of the library are tabulated below. The structures of the individual members of the library may be inferred by reference to the reaction scheme in this Example and FIG. 1.

|   | 1 | 2 | 3 | 4 | 5 | 6 | 7 | 8 | 9 | 10 | 11 | 12 |
|---|---|---|---|---|---|---|---|---|---|----|----|----|
| A | 338; 47% | 324; 84% | 352; 61% | 338; 61% | 334; 63% | 336; 60% | 320; 70% | 352; 53% | 338; 43% | 364; 56% | 385; 44% | 402; 50% |
| B | 340; 52% | 326; 77% | 354; 61% | 340; 55% | 336; 51% | 338; 61% | 322; 48% | 354; 68% | 340; 44% | 366; 50% | 387; 37% | 404; 54% |
| C | 338; 66% | 324; 80% | 352; 61% | 338; 58% | 334; 56% | 336; 60% | 320; 72% | 352; 62% | 338; 48% | 364; 67% | 385; 40% | 402; 57% |
| D | 326; 60% | 312; 67% | 340; 57% | 326; 76% | 322; 66% | 324; 67% | 308; 73% | 340; 77% | 326; 53% | 352; 63% | 373; 35% | 390; 48% |
| E | 366; 47% | 352; 70% | 380; 43% | 366; 70% | 362; 68% | 364; 64% | 348; 39% | 380; 67% | 366; 57% | 392; 55% | 413; 33% | 430; 42% |
| F | 296; 65% | 282; 81% | 310; 75% | 296; 70% | 292; 54% | 294; 90% | 278; 90% | 310; 95% | 296; 56% | 322; 60% | 343; 55% | 360; 52% |
| G | 300; 64% | 286; 88% | 314; 60% | 300; 80% | 296; 52% | 298; 60% | 282; 61% | 314; 68% | 300; 85% | 326; 58% | 347; 33% | 364; 46% |
| H | 272; 56% | 258; 45% | 296; 72% | 272; 59% | 268; 49% | 270; 55% | 254; 66% | 286; 59% | 272; 68% | 298; 49% | 319; 36% | 336; 41% |

The IC$_{50}$ values (μM) against a mammalian anandamide transporter, determined using the anandamide functional assay described in Example 5, of the members of the library are tabulated below. The IC$_{50}$ of AM-404 in this assay was 2.0 μM. The structures of the individual members of the library may be inferred by reference to the reaction scheme in this Example and FIG. 1.

|   | 1 | 2 | 3 | 4 | 5 | 6 | 7 | 8 | 9 | 10 | 11 | 12 |
|---|---|---|---|---|---|---|---|---|---|----|----|----|
| A | <1 | >1 | <1 | <1 | <1 | <1 | <1 | <1 | <1 | <1 | <1 | >1 |
| B | >1 | >1 | >1 | >1 | >1 | >1 | >1 | >1 | >1 | >1 | >1 | >1 |
| C | >1 | >1 | >1 | >1 | >1 | >1 | >1 | >1 | >1 | >1 | >1 | >1 |
| D | >1 | >1 | >1 | >1 | >1 | >1 | >1 | >1 | >1 | >1 | >1 | >1 |
| E | >1 | >1 | >1 | >1 | >1 | >1 | >1 | >1 | >1 | >1 | >1 | >1 |
| F | >1 | >1 | >1 | >1 | >1 | >1 | >1 | >1 | >1 | >1 | >1 | >1 |
| G | >1 | >1 | >1 | >1 | >1 | >1 | >1 | >1 | >1 | >1 | >1 | >1 |
| H | >1 | >1 | >1 | >1 | >1 | >1 | >1 | >1 | >1 | >1 | >1 | >1 |

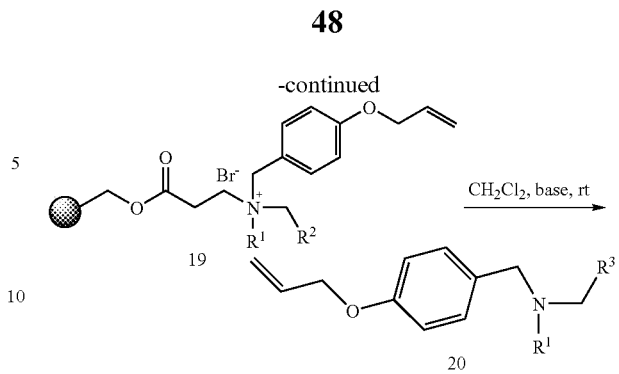

Figure 2:
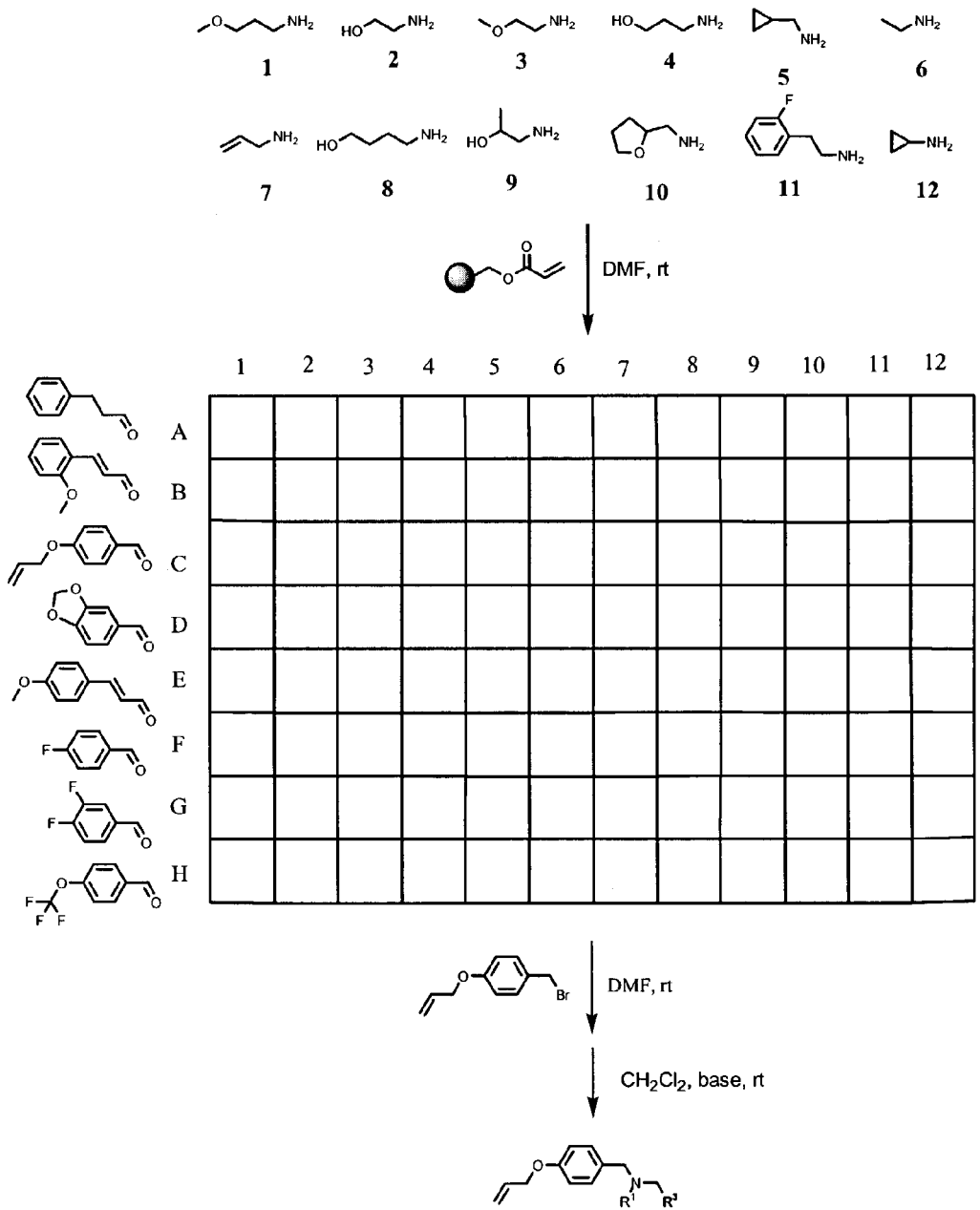
FIG. 2 depicts schematically the synthesis and ninety-six members of a combinatorial library of anandamide transporter inhibitors comprising a 4-allyloxybenzyl moiety.

The combinatorial library depicted schematically in FIG. 2 was prepared according to the reaction scheme above, using the general protocol outlined in Example 3. Accordingly, ninety-six compounds represented by general structure 20 were prepared.

The molecular ion (M+H$^+$) observed in LRMS experiments and the yield obtained for each of the members of the library are tabulated below. The structures of the individual members of the library may be inferred by reference to the reaction scheme in this Example and FIG. 2.

|   | 1 | 2 | 3 | 4 | 5 | 6 | 7 | 8 | 9 | 10 | 11 | 12 |
|---|---|---|---|---|---|---|---|---|---|----|----|----|
| A | 354; 53% | 326; 46% | 340; 58% | 340; 53% | 336; 55% | 310; 50% | 322; 53% | 354; 70% | 340; 54% | 366; 54% | 404; 55% | 322; 36% |
| B | 382; 37% | 354; 47% | 368; 40% | 368; 42% | 364; 38% | 338; 38% | 350; 36% | 382; 41% | 368; 37% | 394; 35% | 432; 30% | 350; 31% |
| C | 382; 30% | 354; 31% | 368; 34% | 368; 31% | 364; 39% | 338; 42% | 350; 30% | 382; 38% | 368; 31% | 394; 33% | 432; 30% | 350; 29% |
| D | 370; 40% | 342; 43% | 356; 44% | 356; 49% | 352; 56% | 326; 44% | 338; 40% | 370; 35% | 356; 34% | 382; 42% | 420; 30% | 338; 29% |
| E | 382; 28% | 354; 43% | 368; 35% | 368; 39% | 364; 38% | 338; 41% | 350; 35% | 382; 42% | 368; 42% | 394; 29% | 432; 32% | 350; 28% |
| F | 344; 29% | 316; 31% | 330; 30% | 330; 31% | 326; 34% | 300; 41% | 312; 28% | 344; 33% | 330; 29% | 356; 39% | 394; 44% | 312; 34% |
| G | 362; 33% | 334; 42% | 348; 45% | 348; 35% | 344; 25% | 318; 36% | 330; 33% | 362; 38% | 348; 32% | 374; 57% | 412; 40% | 330; 30% |
| H | 410; 30% | 382; 36% | 396; 28% | 396; 25% | 392; 47% | 366; 29% | 378; 27% | 410; 33% | 396; 34% | 422; 31% | 460; 29% | 378; 33% |

Example 4

Solid-Phase Synthesis of a Combinatorial Library of Anandamide Transporter Inhibitors Comprising a 4-Allyloxybenzyl Moiety (See FIG. 2)

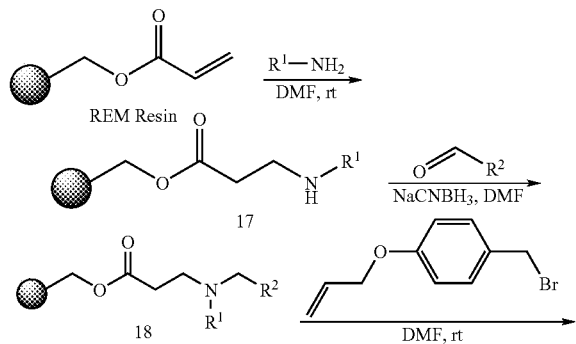

The IC$_{50}$ values (μM) against a mammalian anandamide transporter, determined using the anandamide functional assay described in Example 5, of the members of the library are tabulated below. The IC$_{50}$ of AM-404 in this assay was 2.0 μM. The structures of the individual members of the library may be inferred by reference to the reaction scheme in this Example and FIG. 2.

|   | 1 | 2 | 3 | 4 | 5 | 6 | 7 | 8 | 9 | 10 | 11 | 12 |
|---|---|---|---|---|---|---|---|---|---|----|----|----|
| A | >1 | >1 | >1 | >1 | >1 | >1 | >1 | >1 | >1 | >1 | >1 | >1 |
| B | >1 | >1 | >1 | >1 | >1 | >1 | >1 | >1 | >1 | >1 | >1 | >1 |
| C | >1 | >1 | >1 | >1 | <1 | >1 | <1 | >1 | >1 | >1 | >1 | >1 |
| D | >1 | >1 | >1 | >1 | >1 | >1 | >1 | >1 | >1 | >1 | >1 | >1 |
| E | >1 | >1 | >1 | >1 | >1 | >1 | >1 | >1 | >1 | >1 | >1 | >1 |
| F | >1 | >1 | >1 | >1 | >1 | >1 | >1 | >1 | >1 | >1 | >1 | >1 |
| G | >1 | >1 | >1 | >1 | >1 | <1 | >1 | >1 | >1 | >1 | >1 | >1 |
| H | >1 | >1 | >1 | >1 | >1 | >1 | >1 | >1 | >1 | >1 | >1 | >1 |

Example 5

Solid-Phase Synthesis of 3-(4-{[(2-Methoxy-ethyl)-(3-phenyl-allyl)-amino]-methyl}-phenyl)-acrylic acid (21)

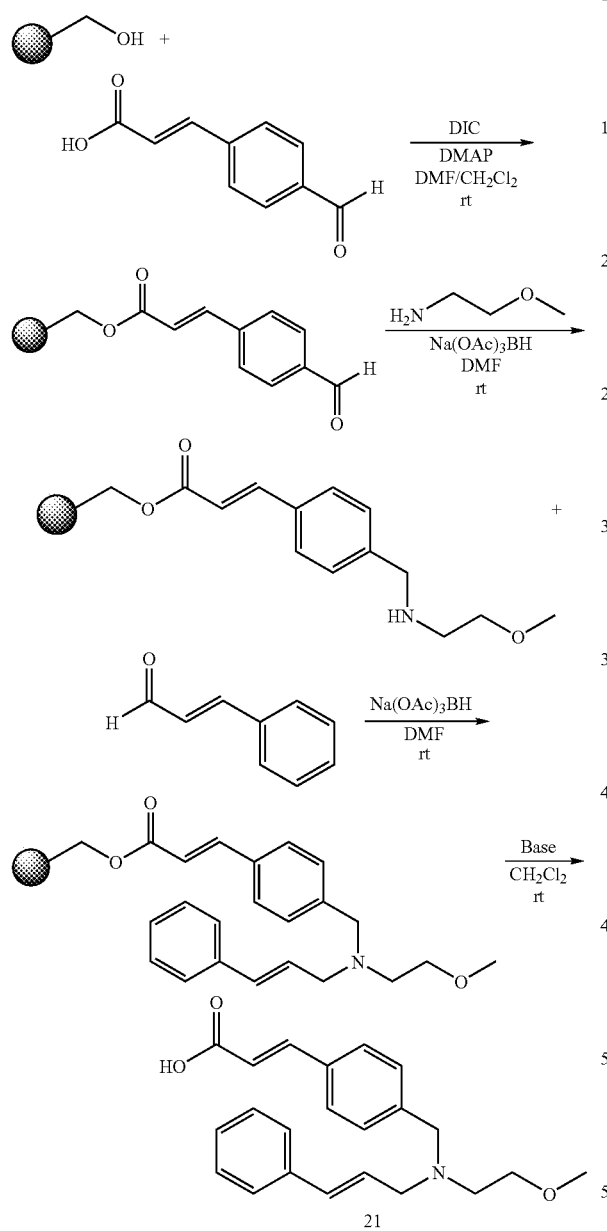

Wang resin (1.1 mmol/g, 1.00 g) in a polypropylene filtration tube with a polyethylene frit was added DMF (5 mL) and CH$_2$Cl$_2$ (5 mL), followed by 4-formylcinnamic acid (5.5 mmol, 969 mg), DMAP (1.08 mmol, 132 mg) and diisopropylcarbodiimide (5.5 mmol, 861 µL). The mixture was shaken at room temperature for 24 hours. The resulting resin was washed with DMF (3×5 mL), MeOH (3×5 mL) and CH$_2$Cl$_2$ (4×5 mL), then dried in vacuo. To the resin (100 mg) was added 2-methoxyethylamine (1.1 mmol, 96 µL) in DMF (1 mL), Na(OAc)$_3$BH (2.2 mmol, 466 mg) and acetic acid (25 µL). After shaking at room temperature overnight, the resulting resin was washed with DMF (3×1 mL), MeOH (3×1 mL) and CH$_2$Cl$_2$ (4×1 mL), then dried in vacuo. The resulting resin was suspended in a solution of trans-cinnamaldehyde (1.1 mmol, 139 µL), Na(OAc)$_3$BH (2.2 mmol, 466 mg) and acetic acid (10 µL) in DMF (1 mL). The mixture was shaken at room temperature for 24 hours. The resulting resin was washed with DMF (3×1 mL), MeOH (3×1 mL) and CH$_2$Cl$_2$ (4×1 mL), then dried in vacuo. To the dry resin was added polyamine resin and CH$_2$Cl$_2$. The mixture was agitated at room temperature for 24 hours, then filtered and washed with CH$_2$Cl$_2$ (2×1.5 mL). The filtrates were collected and evaporated to yield 21 as a colorless oil (LRMS m/z 351).

Example 6

Anandamide Uptake Functional Assay

The characterization of anandamide uptake was performed with human monocytes (U-937 cells), using a 96 wells format (volume of the reaction 500 µL). Uptake of radiolabelled anandamide by U-937 cells (10$^5$ cells in 400 µL/well) occured during a 15 minutes incubation time at 37° C. in the presence of test compounds added in solution in 50 µL and 50 µL of [$^3$H]-AEA (2 nM)/AEA (98 nM).

U-937 cells and [$^3$H]-AEA/AEA were prepared in a Krebs buffer pH 7.4 containing 25 mM NaHCO$_3$, 11 mM glucose, 50 µM ascorbic acid and 1% BSA. This incubation buffer is oxygenated for 5 minutes before incubation. Basal control is incubated for 15 minutes at 4° C., in absence of any test or reference compound to prevent uptake.

Following incubation, uptake was stopped by filtration through a "unifilter 96-well GFB plate" (Packard) washed with Krebs buffer containing 25 mM NaHCO$_3$ to eliminate the free [$^3$H]-AEA. The radioactivity associated with the U-937 cells corresponding to the uptake was retained on the unifilter and was measured with a Topcount Microplate Scintillation Counter, (Packard) using Microscint 0 scintillation liquid (Packard).

FIGS. 3–5 depict certain compounds of the present invention and their IC$_{50}$ values as determined in this assay. The reference compound, AM404, which was used a standard, was tested at ten concentrations ranging from 10$^{-9}$ M to 10$^{-4}$ M to obtain an IC$_{50}$ value. See generally Maccarrone, M. et al. "Anandamide hydrolysis by human cells in culture and brain" *J. Biol. Chem.* 1998, 273: 32332–32339; and Muthian, S. et al. *J. Pharmacol. Exp. Ther.* 2000, 293, 289–295.

Example 7

Figure 6:
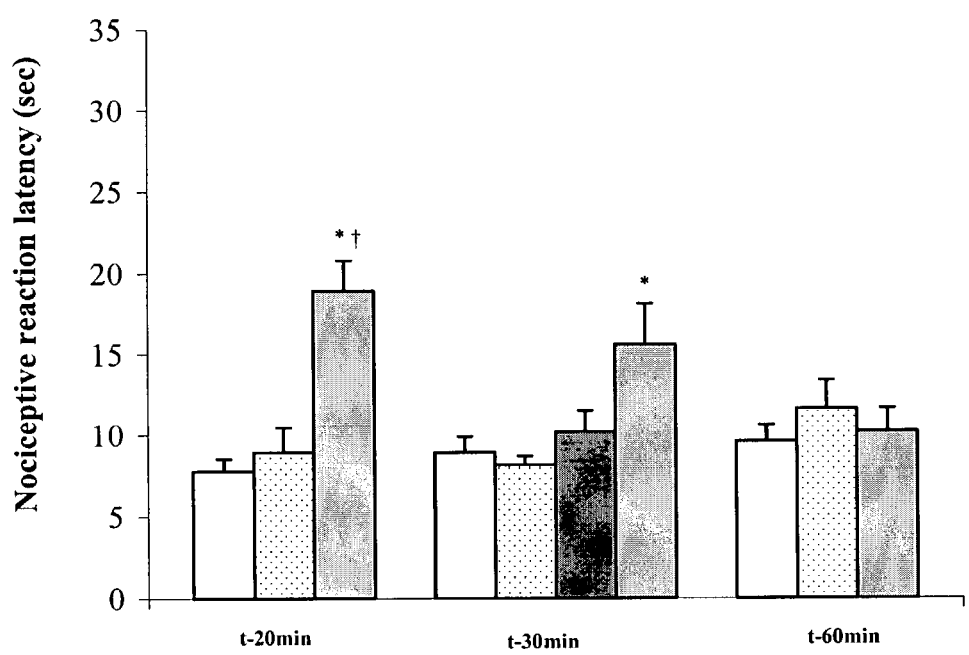
FIG. 6 depicts graphically the anti-nociceptive effects in vivo of anandamide and a compound of the present invention separately and in combination. See Example 7.

Anti-Nociceptive Effects In Vivo of Anandamide and Compound 4 Separately and in Combination (See FIG. 6)

Overview

This experiment assessed the analgesic effects of anandamide, compound 4, and a combination of anadamide and compound 4 in the hot plate test in mice.

Test System

One hundred (100) male Swiss mice ICO: OF1 (IOPS Caw) (Iffa Credo, France) weighing 17 g to 23 g were used in the study. The mice were housed in a temperature (19.5–24.5° C.) and relative humidity (45–65%) controlled room with a 12-h light/dark cycle, with ad libitum access to filtered tap-water and standard pelleted laboratory chow (U.A.R., France) throughout the study. Upon receipt at animal facilities, they were housed 20 per cage and at least a 5-day acclimatization period was observed. Animals were individually identified on their tails.

Materials Used

Anandamide

Compound 4

Vehicle=0.9% NaCl with 20% DMSO

Equipment=Hot plate (Socrel model DS37; Ugo Basile, Italy)

Principal Data Processing System=SigmaStat® v. 2.0.3 (SPSS Science Software, Erkrath GmbH)

Study Design

Ten groups of 10 animals each were used in this study. The individual groups were treated as set forth below. The doses used are expressed in terms of free active substance. The test and reference substances and the vehicle were administered by intravenous route (i.v) in a random order with a volume of 5 mL/kg. Anandamide and compound 4 were concomitantly administered as a mixture by intravenous route under a volume of 10 mL/kg (Groups 3, 7 and 10).

Group 1: vehicle (t=20 minutes)

Group 2: Anandamide (20 mg/kg) (t=20 minutes)

Group 3: Anandamide (20 mg/kg)+Compound 4 (10 mg/kg) (t=20 minutes)

Group 4: vehicle (t=30 minutes)

Group 5: Anandamide (20 mg/kg) (t=30 minutes)

Group 6: Compound 4 (10 mg/kg) (t=30 minutes)

Group 7: Anandamide (20 mg/kg)+Compound 4 (10 mg/kg) (t=30 minutes)

Group 8: vehicle (t=60 minutes)

Group 9: Anandamide (20 mg/kg) (t=60 minutes)

Group 10: Anandamide (20 mg/kg)+Compound 4 (10 mg/kg) (t=60 minutes)

Experimental Protocol

Twenty, thirty and sixty minutes after dosing, a given mouse was placed on a metallic hot plate maintained at 56±0.2° C. The nociceptive reaction latency, characterized by a licking reflex of the forepaws or by a jumping off the hot plate, was recorded. The cut-off time was set to 30 seconds. See Eddy NB, Touchberry CF, Lieberman JE. "Synthetic analgesics. 1-Methadone isomers and derivatives" *J.Pharmacol.Exp.Ther.* 1950; 98:121–137; and Beltramo M, Stella N, Calignano A, Lin SY, Makriyannis A, Piomelli D. "Functional role of high-affinity anandamide transport, as revealed by selective inhibition" *Science* 1997; 277:1094–1097.

Results

The raw data is presented below. The mean results from these experiments are presented graphically in FIG. 6. The results tabulated in FIG. 6 are expressed as mean±sem. ANOVA (2 ways): time/treatment's effect as well as interaction between the two, for vehicle, anandamide and association groups. Dunnett's test: * indicates a significant difference in comparison with the vehicle-treated group for $P<0.05$. Dunnett's test :† indicates a significant difference in comparison with the same treated group at t–60 min for $P<0.05$. ANOVA (1 ways): at t–30 min for vehicle, anandamide, compound 4 and association groups. Dunnett's test: ° indicates a significant difference in comparison with the vehicle-treated group for $P<0.05$. Vehicle: Saline+20% DMSO; n=10 mice per groups.

Nociceptive Reaction Latency (Seconds)

| time = 20 minutes post-administration (columns 1, 2 and 3 of FIG. 6, respectively) | | | |
|---|---|---|---|
| | Vehicle | Anandamide (20 mg/kg) | Anandamide (20 mg/kg) + Compound 4 (10 mg/kg) |
| | 5.4 | 7.8 | 16.7 |
| | 7.6 | 5.1 | 11.1 |
| | 8 | 11.5 | 10 |
| | 5.8 | 10.3 | 15.2 |
| | 11 | 21.2 | 20 |
| | 9.3 | 6.3 | 23.4 |
| | 6.3 | 8.8 | 21.2 |
| | 7.1 | 4.9 | 19.5 |
| | 5.7 | 5.3 | 30 |
| | 11.8 | 8.1 | 22 |
| Mean | 7.8 | 8.9 | 18.9 |
| S.E.M. | 0.7 | 1.5 | 1.9 |
| N | 10 | 10 | 10 |

| time = 30 minutes post-administration (columns 4, 5, 6 and 7 of FIG. 6, respectively) | | | | |
|---|---|---|---|---|
| | Vehicle | Anandamide (20 mg/kg) | Compound 4 (10 mg/kg) | Anandamide (20 mg/kg) + Compound 4 (10 mg/kg) |
| | 15.3 | 7.1 | 13.5 | 11.3 |
| | 9.4 | 6.5 | 16.3 | 30 |
| | 6.5 | 7.8 | 6.1 | 7 |
| | 7 | 8.9 | 10 | 16 |
| | 8.7 | 7.5 | 12.8 | 11 |
| | 7 | 10.7 | 14.5 | 12.3 |
| | 12.5 | 7.9 | 4.5 | 12.9 |
| | 5.4 | 5.2 | 10.4 | 22.2 |
| | 7.5 | 9.7 | 4.2 | 6.9 |
| | 9.9 | 10 | 9.6 | 26.3 |
| Mean | 8.9 | 8.1 | 10.2 | 15.6 |
| S.E.M. | 1.0 | 0.5 | 1.3 | 2.5 |
| N | 10 | 10 | 10 | 10 |

| time = 60 minutes post-administration (columns 8, 9 and 10 of FIG. 6, respectively) | | | |
|---|---|---|---|
| | Vehicle | Anandamide (20 mg/kg) | Anandamide (20 mg/kg) + Compound 4 (10 mg/kg) |
| | 11.5 | 13.5 | 12.2 |
| | 7.5 | 24.4 | 9.7 |
| | 13.3 | 4.6 | 6.8 |
| | 13.5 | 6.9 | 11.6 |
| | 9.5 | 11.1 | 14.2 |
| | 5.9 | 10.1 | 6.9 |
| | 6.4 | 9.3 | 20.6 |
| | 7.5 | 11.7 | 7 |
| | 14.3 | 8.9 | 6 |
| | 6.5 | 16.1 | 7.3 |
| Mean | 9.6 | 11.7 | 10.2 |
| S.E.M. | 1.0 | 1.7 | 1.4 |
| N | 10 | 10 | 10 |

INCORPORATION BY REFERENCE

All of the patents and publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A compound represented by A:

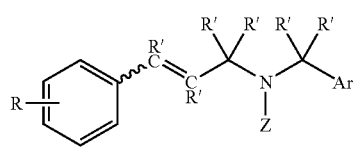

wherein
- Z represents alkyl, cycloalkyl, alkenyl, aralkyl, heteroaralkyl, hydroxyalkyl, alkoxyalkyl, heterocyclyl, —$(CH_2)_n$—$R_{80}$, or a covalent tether to a solid support;
- Ar represents substituted aryl;
- R is absent or present 1, 2, 3, 4, or 5 times;
- R represents independently for each occurrence alkyl, cycloalkyl, alkenyl, alkynyl, aryl, heteroaryl, aralkyl, halogen, heteroaralkyl, hydroxyl, alkoxyl, amino, alkylamino, carboxylate, carboxamide, nitroso, nitro, sulfhydryl, alkylthio, thioalkyl, silyl, alkylsulfonyl, arylsulfonyl, formyl, acyl, acyloxy, acylamino, alkyloxycarbonyl, alkenyloxycarbonyl, aryloxycarbonyl, or —$(CH_2)_n$—$R_{80}$;
- R' represents independently for each occurrence H, alkyl, cycloalkyl, aryl, heteroaryl, aralkyl, heteroaralkyl, or —$(CH_2)_n$—$R_{80}$;
- $R_{80}$ represents independently for each occurrence cycloalkyl, alkenyl, aryl, heteroaryl, or heterocyclyl;
- n is an integer selected independently for each occurrence from the range 0 to 8 inclusive;
- the absolute stereochemistry at a stereocenter in a compound represented by A is R, S, or a mixture thereof; and
- the configuration of an alkenyl moiety in a compound represented by A is E, Z, or a mixture thereof.

2. The compound of claim 1, wherein Z represents 2-methoxyethyl, 2-hydroxyethyl, 3-methoxypropyl, 3-hydroxypropyl, cyclopropyl, cyclopropylmethyl, 2-methylpropyl, butyl, allyl, 4-hydroxybutyl, 2-hydroxypropyl, (tetrahydrofuran-2-yl)methyl, 2-(pyrid-4-yl)ethyl, or 2-(2-fluorophenyl)ethyl.

3. The compound of claim 1, wherein Ar represents 4-allyloxyphenyl, 4-propyloxyphenyl, 2-allyloxyphenyl, 3,4-(methylenedioxy)phenyl, 4-(trifluoromethoxy)phenyl, 4-methylphenyl, 4-methoxyphenyl, 4-carboxyphenyl, or 4-fluorophenyl.

4. The compound of claim 1, wherein R is absent.

5. The compound of claim 1, wherein R' represents H.

6. The compound of claim 1, wherein Z represents 2-methoxyethyl, 2-hydroxyethyl, 3-methoxypropyl, 3-hydroxypropyl, cyclopropyl, cyclopropylmethyl, 2-methylpropyl, butyl, allyl, 4-hydroxybutyl, 2-hydroxypropyl, (tetrahydrofuran-2-yl)methyl, 2-(pyrid-4-yl)ethyl, or 2-(2-fluorophenyl)ethyl; and Ar represents 4-allyloxyphenyl, 4-propyloxyphenyl, 2-allyloxyphenyl, 3,4-(methylenedioxy)phenyl, 4-(trifluoromethoxy)phenyl, 4-methylphenyl, 4-methoxyphenyl, 4-carboxyphenyl, or 4-fluorophenyl.

7. The compound of claim 1, wherein Z represents 2-methoxyethyl, 2-hydroxyethyl, 3-methoxypropyl, 3-hydroxypropyl, cyclopropyl, cyclopropylmethyl, 2-methylpropyl, butyl, allyl, 4-hydroxybutyl, 2-hydroxypropyl, (tetrahydrofuran-2-yl)methyl, 2-(pyrid-4-yl)ethyl, or 2-(2-fluorophenyl)ethyl; Ar represents 4-allyloxyphenyl, 4-propyloxyphenyl, 2-allyloxyphenyl, 3,4-(methylenedioxy)phenyl, 4-(trifluoromethoxy)phenyl, 4-methylphenyl, 4-methoxyphenyl, 4-carboxyphenyl, or 4-fluorophenyl; and R is absent.

8. The compound of claim 1, wherein Z represents 2-methoxyethyl, 2-hydroxyethyl, 3-methoxypropyl, 3-hydroxypropyl, cyclopropyl, cyclopropylmethyl, 2-methylpropyl, butyl, allyl, 4-hydroxybutyl, 2-hydroxypropyl, (tetrahydrofuran-2-yl)methyl, 2-(pyrid-4-yl)ethyl, or 2-(2-fluorophenyl)ethyl; Ar represents 4-allyloxyphenyl, 4-propyloxyphenyl, 2-allyloxyphenyl, 3,4-(methylenedioxy)phenyl, 4-(trifluoromethoxy)phenyl, 4-methylphenyl, 4-methoxyphenyl, 4-carboxyphenyl, or 4-fluorophenyl; R is absent; and R' represents H.

9. The compound of claim 1, wherein said compound has an $IC_{50}$ less than 1 µM in an assay based on a mammalian anandamide transporter.

10. The compound of claim 1, wherein said compound has an $IC_{50}$ less than 100 nM in an assay based on a mammalian anandamide transporter.

11. The compound of claim 1, wherein said compound has an $IC_{50}$ less than 10 nM in an assay based on a mammalian anandamide transporter.

12. The compound of claim 1, wherein said compound has an $EC_{50}$ less than 1 µM in an assay based on a mammalian anandamide transporter.

13. The compound of claim 1, wherein said compound has an $EC_{50}$ less than 100 nM in an assay based on a mammalian anandamide transporter.

14. The compound of claim 1, wherein said compound has an $EC_{50}$ less than 10 nM in an assay based on a mammalian anandamide transporter.

15. The compound of claim 1, wherein said compound is a single stereoisomer.

16. A formulation, comprising a compound of claim 1; and a pharmaceutically acceptable excipient.

* * * * *